US006893627B2

(12) United States Patent
Ribnicky et al.

(10) Patent No.: US 6,893,627 B2
(45) Date of Patent: May 17, 2005

(54) **METHOD FOR TREATING TYPE 2 DIABETES WITH AN EXTRACT OF *ARTEMISIA***

(75) Inventors: David M. Ribnicky, Plainsboro, NJ (US); Ilya Raskin, Manalapan, NJ (US)

(73) Assignee: Rutgers, The State University of New Jersey, Middlesex, NJ (US)

( * ) Notice: Subject to any disclaimer, the term of this patent is extended or adjusted under 35 U.S.C. 154(b) by 84 days.

(21) Appl. No.: 10/232,756

(22) Filed: Aug. 30, 2002

(65) Prior Publication Data

US 2003/0072822 A1 Apr. 17, 2003

Related U.S. Application Data

(60) Provisional application No. 60/316,760, filed on Aug. 31, 2001.

(51) Int. Cl.[7] .............................................. A61K 35/78
(52) U.S. Cl. ..................................................... 424/7.25
(58) Field of Search .............................. 424/195.1, 725

(56) References Cited

U.S. PATENT DOCUMENTS

| | | | |
|---|---|---|---|
| 4,534,317 | A | 8/1985 | Walsh et al. |
| 6,096,364 | A | 8/2000 | Bok et al. |
| 6,251,380 | B1 | 6/2001 | Jo |

FOREIGN PATENT DOCUMENTS

| | | |
|---|---|---|
| WO | WO 97/35598 | 10/1997 |
| WO | WO 00/15174 | 2/2000 |

OTHER PUBLICATIONS

Subramoniam et al. Effects of Artemisia Pallens Wall. On Blood Glucose Levels in Normal and Alloxan–Induced Diabetic Rats; Jornal of Ethanopharmacology 50 (1996) 13–17.*

International Search Report, United States Patent and Trademark Office, Jan. 14, 2003.
Al–Waili et al., "Treatment of Diabetes Mellitus by *Artemisia Herba–Alba* Extract: Preliminary Study." Clinical and Experimental Pharmacology and Physiology 13:569–573 (1986).
Ames et al., "Methods for Detecting Carcinogens and Mutagens with the Salmonella/Mammalian–Microsome Mutagenicity Test." Mutation Res. 31:347–364 (1975).
Drucker, "Glucagon–Like Peptides," Diabetes 47:159–169 (1998).
Fehmann et al., "Cell and Molecular Biology of the Incretin Hormones Glucagon–Like Peptide–and Glucose–Dependent Insulin Releasing Polypeptide," Endocr. Rev. 16:390–410 (1995).
Henry et al., "Insulin Action and Glucose Metabolism in Nondiabetic Control and NIDDM Subjects." Diabetes 44:936–946 (1995).

(Continued)

*Primary Examiner*—Patricia Leith
(74) *Attorney, Agent, or Firm*—Marshall, Gerstein & Borun LLP

(57) ABSTRACT

The present invention provides materials and methods relating to mildly polar fluid extracts of plant materials, such as *Artemisia* plant species, useful in methods for treating diabetes and methods for modulating the activity of glucagon-like peptide-1 (GLP-1), and in methods for modulating phosphoenol pyruvate carboxykinase (PEPCK) activity in a diabetes-specific manner. The extracts are generally non-toxic and non-mutagenic and may be administered to diabetics with beneficial effect on blood glucose levels. The extracts may also be administered to non-diabetics without deleterious effect. The plants are easily grown with a minimum of time, labor, and cost. Extracts are inexpensively and quickly prepared without the need for fractionation to remove potentially deleterious compounds, and the extracts may be administered to mammals such as humans through various routes, in a variety of forms, and at convenient concentrations.

9 Claims, 17 Drawing Sheets

OTHER PUBLICATIONS

Koch et al., "Partial Purification of the Solubilized Insulin Receptor from Rat Liver Membranes by Precipitation with Concanavalin A," Hoppe–Syler's Z. Physiol. Chem. 362, S:347–351 (1981).

Luna et al., "Oral Agents in the Management of Type 2 Diabetes Mellitus." Am. Fam. Physician 63:1747–1756 (2001).

Piller et al., "Properties and stabilization of an extracellular α–glucosidase from the extremely thermophilic archaebacteria *Thermocccus* strain AN1:enzyme activity at 130° C.," Biochimica et Biophysica Acta 1292:197–205 (1996).

Rodbell, "Metabolism of Isolated Fat Cells," J. Biol. Chem. 239:375–380 (1964).

Sandhu et al., "Glucagon–Like Peptide 1 Increases Insulin Sensitivity in Depancreatized Dogs," Diabetes 48:1045–1053 (1999).

Shimura et al., "Docosahexanoic Acid (DHA) Improved Glucose and Lipid Metabolism in KK–A$^y$ Mice with Genetic Non–Insulin–Dependent Diabetes Mellitus (NIDDM)," Biol. Pharm. Bull. 20:507–510 (1997).

Suto et al., "Genetic analysis of non–insulin–dependent diabetes mellitus in KK and KK–A$^y$ mice," Euro. J. Endocrin. 139:654–661 (1998).

Swanston–Flatt et al., "Evaluation of Traditional Plant Treatments for Diabetes Studies in Streptozotocin Diabetic Mice," Acta Diabetol. Lat. 26:51–55 (1989).

Swanston–Flatt et al . "Traditional dietary adjuncts for the treatment of diabetes mellitus," Proc. Nutr. Soc. 50:641–651(1991).

Tokunaga et al., "Streptozotocin–Induced Elevation of Pancreatic Taurine Content and Suppressive Effect of Taurine on Insulin Secretion," European J. of Pharmacol. 87:237–243 (1983).

Wang et al., "Glucagon–like Peptide–1 Regulates the Beta Cell Transcription Factor, PDX–1, in Insulinoma Cells," Endocrinology 140:4904–4907 (1999).

Yazdanparast et al., "Effects of aqueous tarragon, *Artemisia dracunculus*, extract on lipid and coagulatory parameters in rats," Biomedical Letters 59:137–141 (1999).

\* cited by examiner

Male Body Weight Data for Rats Fed *Artemisia dracunculus* Extract

Female Body Weight Data for Rats Fed *Artemisia dracunculus* Extract

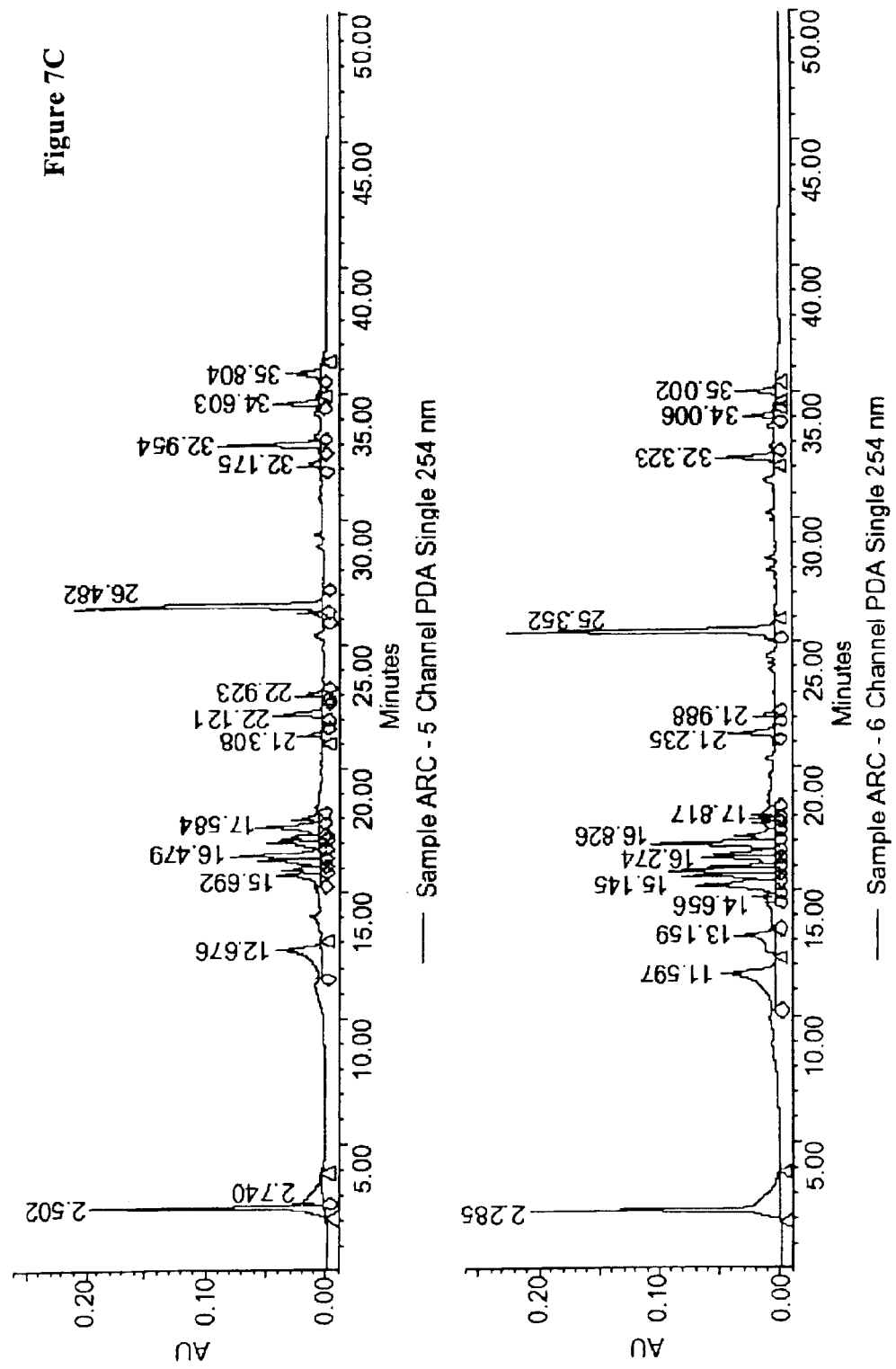

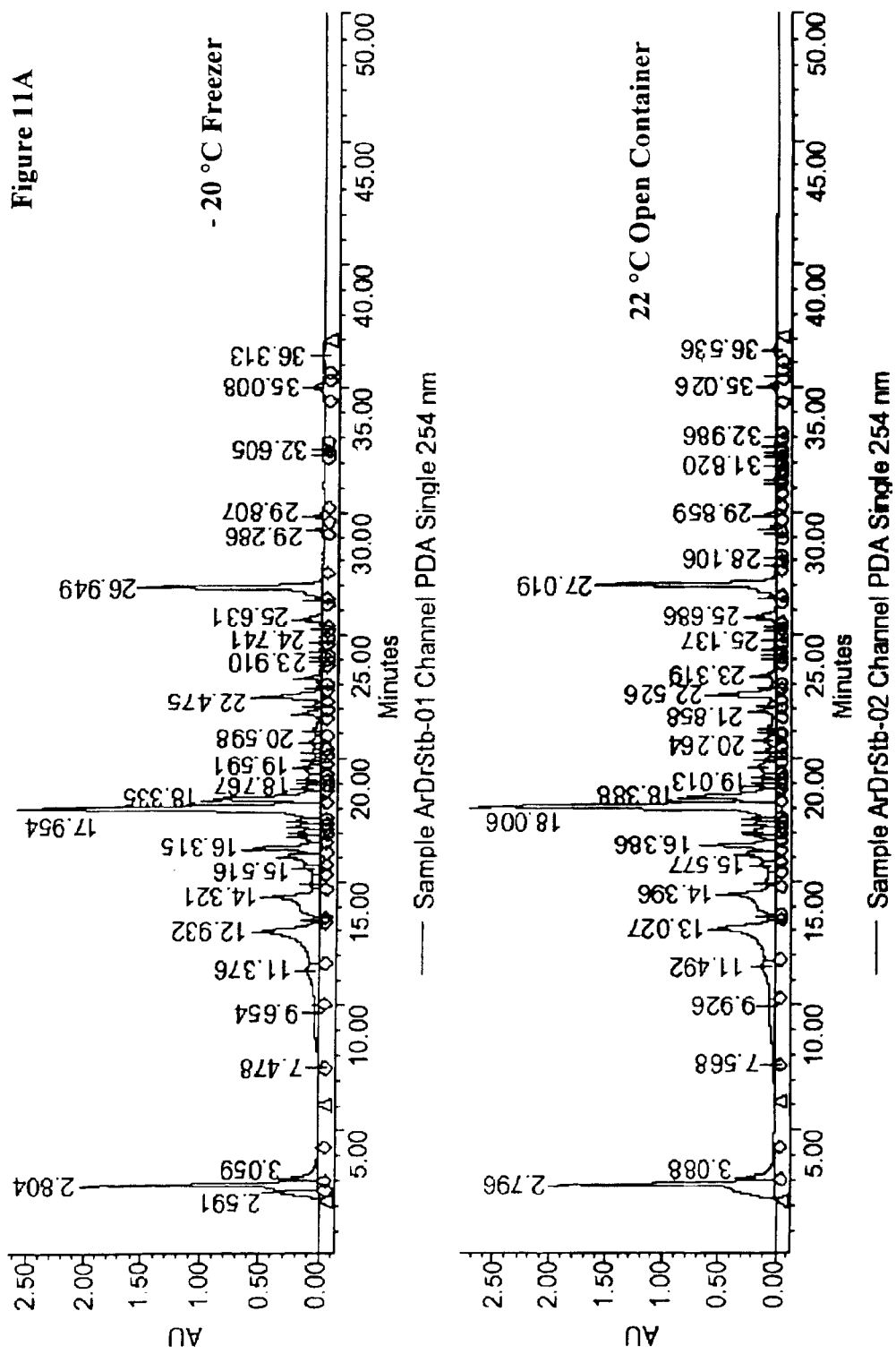

METHOD FOR TREATING TYPE 2 DIABETES WITH AN EXTRACT OF ARTEMISIA

RELATED APPLICATIONS

This application claims benefit of U.S. Provisional Patent Application Ser. No. 60/316,760 filed Aug. 31, 2001, which is incorporated herein by reference in its entirety.

FIELD OF INVENTION

The present invention relates to materials and methods for treating a disorder using plants. More specifically, the invention relates to materials and methods for treating a disorder using extracts of the plant genus *Artemisia*.

BACKGROUND

Diabetes is a major health concern, as evidenced by the number of people it affects as well as the costs incurred in treating or preventing it. According to the American Diabetes Association, there are 15.7 million people, or 5.9% of the U.S. population, that suffer from diabetes. Only about 10.3 million of these people have been diagnosed with the disease. With approximately 5.4 million people unaware that they have this chronic condition, diabetes ranks as the seventh leading cause of death in the U.S. The costs associated with efforts to treat and/or to prevent the condition are commensurate with the number of people afflicted, both in the U.S. and throughout the world.

Diabetes is a complex condition or disease that is most commonly defined by elevated concentrations of blood glucose, with the disorder affecting the metabolism of carbohydrates, fats and proteins. The disorder results from an inability to control blood glucose levels, for example due to insufficient levels or activity of insulin. Elevated glucose levels, in turn, often lead to secondary health problems that require additional medical treatment. Some of the leading diabetes-related health risks include hyperglycemia, arteriosclerosis, diabetic retinopathy (possibly leading to blindness), cataracts, nephropathy, increased risk of infections, hypertension, nerve disease, risk of amputations, impotence, diabetic ketoacidosis, and dementia. While these health risks are associated with diabetes, they are not, by themselves, useful indicators of diabetes. For example, hypertension may occur with or without diabetes (e.g., due to a genetic predisposition or a high-salt diet).

There are two primary types of diabetes, with many variations of each. Type 1 diabetes generally occurs in childhood and results from the body's inability to produce insulin. Type 2 diabetes is the more prevalent form and results from either insulin deficiency or, more commonly, from insulin resistance. Some diabetics are able to maintain healthy blood glucose concentrations with restrictive diets alone, but most require the assistance of oral hypoglycemic drugs and/or insulin replacement therapy by injection. Drug therapy, however, does not always achieve satisfactory glycemic control and insulin use often promotes hypoglycemia. Moreover, these conventional treatments often lower blood glucose by promoting the non-selective uptake of glucose by many cells, including adipocytes, which contributes to undesirable weight gain. Therefore, continuous treatment modifications and monitoring are often necessary. Additionally, traditional treatments, like insulin injections, are expensive and can be painful to administer.

In addition to conventional treatments relying on insulin injections or over-the-counter medications, natural products, including plant materials, have been reportedly tried in alternative treatments of conditions such as diabetes. This is perhaps unsurprising, given the great variety of plants in the world. As traditional medicines, plants have been used for a variety of real or imagined ailments, with the same plants frequently being used to "treat" unrelated conditions. One of the many plant families used in traditional herbal remedies is the *Artemisia* family, with over 400 different species.

One species of *Artemisia*, *Artemisia dracunculus*, Yazdanparast et al., *Biomedical Letters* 59:137–141 (1999) has been reported to yield alcohol-based extracts that exhibit an antihyperlipidemic effect on rats fed high-fat diets. The authors of this study did not, however, test for the presence of mutagens or toxins and did not explore the use of such extracts to treat disorders, diseases or conditions other than hyperlipidemia. *A. dracunculus* and another *Artemisia* species, *Artemisia herba-alba*, have been reportedly used to treat headaches and dizziness, e.g., in Middle Eastern cultures. [Al-Waili et al., *Clinical and Experimental Pharmacology and Physiology* 13:569–573 (1986)]. Additionally, Swanston-Flatt et al., *Proc. Nutr. Soc.* 50: 641–651 (1991) disclosed the use of tarragon mixtures in treating diabetes, referencing Swanston-Flatt et al., *Acta Diabetol. Lat.* 26:51–55 (1989), for an explanation that treatments were prepared by mixing homogenized plant material into standard diets. Extracts were never prepared from the tarragon. Swanston-Flatt et al. (1991) reported that tarragon, while reportedly shown to reduce body weight, polydipsia and hyperphagia, did not significantly lower blood glucose concentrations.

Along with the reported medicinal effects of the *Artemisia* spp, however, is the observation that crude extracts prepared from *Artemisia* spp have a positive mutagenic effect when tested in a conventional Ames mutagenicity test. PCT Publication WO 97/35598 describes aqueous (i.e., water) extracts of *Artemisia judaica* as having an insulinomimetic anti-diabetic effect, but also notes the presence of a deleterious mutagen that would render the crude extract unsuitable for administration to mammals such as humans. WO 97/35598 reported that two different preparations from *Artemisia judaica* tested positive in the Ames test for mutagenicity. Therefore, not all *Artemisia* plants, e.g., not *A. judaica*, appear suitable for use in extracts for treating mammals having a disorder such as diabetes.

Thus, there remains a need in the art to develop methods of alleviating, preventing or treating symptoms of diabetes, or the disorder itself, and the health risks associated with diabetes, preferably methods based on the use of readily available and inexpensively produced natural materials such as plants or plant parts. The methods should be both effective and inexpensive without introducing unwarranted toxicity and/or mutagenicity risks. There is also a need to develop methods that modulate enzymes involved in glucose metabolism to facilitate the control of diabetic and non-diabetic symptoms involved in a variety of disorders and diseases found in mammals. There further remains a need to develop an effective method of extracting materials useful for treating diabetes or symptoms of diabetes from a plant or portions of a plant. Additionally, there is a need in the art for methods of controlling body weight, for example in conjunction with diabetes therapies. It is also apparent that for diabetics, athletes, and others, there is a need for increasing the energy store available to a cell, e.g., a muscle cell or neuron.

SUMMARY OF THE INVENTION

The present invention satisfies one or more of the aforementioned needs in the art by providing convenient methods of obtaining extracts from plants such as members of the genus *Artemisia*. The present invention also provides a safe and effective method for the use of plant extracts, such as *Artemisia* extracts, in modulating blood glucose levels and in modulating protein activities involved in carbohydrate metabolism, including effective methods to control blood glucose levels by modulating the activity of glucagon-like peptide-1 (GLP-1). Also provided is a method of increasing glucose uptake in non-adipose cells of mammals, such as muscle cells and neurons. Also contemplated are methods for modulating insulin receptor substrate 2 (IRS-2), methods for modulating insulin-stimulated glucose uptake, methods for the diabetic-specific modulation of hepatic glucose output and phosphoenol pyruvate carboxykinase (PEPCK) activity, methods for decreasing insulin resistance; methods for treating Type 2 diabetes, methods for preparing an aqueous (ie. highly polar, such as water) or mildly polar extract of *Artemisia*, methods for controlling weight gain, methods for increasing the energy store of a cell (e.g., intracellular glucose available to non-adipocyte cells such as muscle cells and neurons) and pharmaceutical compositions comprising an effective dose of an extract of *Artemisia*.

The present invention provides a method of modulating glucagon-like peptide-1 (GLP-1) activity in a mammal comprising administration of an effective dose of an alcoholic extract of *Artemisia*. GLP-1 is encoded by a proglucagon gene and is known to inhibit gastric emptying, control food intake, stimulate insulin biosynthesis and secretion, inhibit glucagon secretion, cause islet proliferation, promote an ileal brake, and regulate hypothalamic-pituitary function. Preferably, GLP-1 activity is increased or enhanced. The GLP-1 activity may be increased by increasing the affinity of GLP-1 for its native receptor, which enhances various activities of GLP-1 known to help lower blood glucose, such as inhibiting gastric emptying, controlling food intake, stimulating insulin biosynthesis and secretion, inhibiting glucagon secretion, enhancing islet proliferation, and promoting an ileal brake. A preferred GLP-1 activity that can be modulated is the controlling of food intake or satiety. Another preferred GLP-1 activity that can be modulated is promotion of an ileal brake, which inhibits gastric and pancreatic secretions and prevents gastric emptying. The contemplated mammal to receive administration of the extract comprises human, dog, cat, horse, cattle, pig, sheep, and other mammals. A preferred mammal to receive administration of the extract is a human. Various routes of administration can be used to deliver the extract to a patient, including injection (e.g., intravenous, intramuscular and subcutaneous), sublingual administration, oral administration, topical administration, and inhalation. Preferably, the route of administration is oral, e.g., a bolus or solution for ingestion. Also preferred is delivery through a nasogastric tube.

A variety of mildly polar fluids, such as alcohols, can be used to extract efficacious materials from plants such as *Artemisia* species (e.g., *Artemisia dracunculus*), including methanol, ethanol, and isopropanol. A preferred alcohol used to extract efficacious materials from *Artemisia dracunculus* is ethanol, thereby producing an ethanolic extract. Preferably, the extract lacks mutagenic activity and/or toxins. The extract can be derived from one of a number of *Artemisia* species including *dracunculus, vulgaris, abysinica, absynthicum, aftra, cannariensis, scoparia*, and others. Preferably, the extract is derived from *A. dracunculus*.

The invention further provides a method of modulating blood glucose levels in a mammal comprising administration of an effective dose of an alcoholic extract of a plant, such as *Artemisia dracunculus*, wherein the alcoholic extract lacks mutagenic activity when assayed using an Ames test (Ames et al., *Mutation Res.* 31:347 (1975)). The Ames test is well-known in the art as a test used to determine the mutagenic properties of substances using bacteria. In such methods, a preferred alcoholic extract has no acute oral toxicity at a dosage of up to 5000 milligrams extract per kilogram mammal body weight (mg/kg). A variety of alcohols can be used to extract efficacious materials from *Artemisia dracunculus*, including methanol, ethanol, and isopropanol. A preferable alcohol used to extract efficacious materials from *Artemisia dracunculus* is ethanol. Preferably, the blood glucose levels are lowered or reduced. The contemplated mammal to receive administration of the extract comprises human, dog, cat, horse, cattle, pig, and sheep, with a human being preferred. Various routes of administration can be used to deliver the extract to a patient including injection (e.g., intravenous, intramuscular and subcutaneous), administration via a nasogastric tube, sublingual administration, oral administration, topical administration and inhalation. Preferably, the route of administration is oral, e.g., a bolus or solution for ingestion. Also preferred is delivery through a nasogastric tube.

In one aspect, the invention provides a method of modulating blood glucose level in a mammal comprising administration of an effective dose of a mildly polar extract of a plant such as *Artemisia*. Preferably, blood glucose level is decreased.

In another aspect, the invention provides a method of modulating GLP-1 activity in a mammal comprising administration of an effective dose of a mildly polar extract of a plant such as *Artemisia*. Preferably, GLP-1 activity is increased.

Another aspect of the invention provides a method of altering the appetite of a mammal comprising administration of an effective dose of a mildly polar extract of a plant such as *Artemisia*.

A further aspect of the invention provides a method of promoting an ileal brake in a mammal comprising administration of an effective dose of a mildly polar extract of a plant such as *Artemisia*.

In another aspect, the invention provides a method of modulating the binding between GLP-1 and the GLP-1 receptor in a mammal comprising administration of an effective dose of a mildly polar extract of a plant such as *Artemisia*. Preferably, the binding of GLP-1 to its receptor is increased.

An additional aspect of the invention provides a method of modulating α-glucosidase activity in a mammal comprising administration of an effective dose of a mildly polar extract of a plant such as *Artemisia*. Preferably, α-glucosidase activity is decreased.

In another aspect, the invention provides a method of modulating insulin resistance in a mammal comprising administration of an effective dose of an alcoholic extract of a plant such as *Artemisia*. Preferably, insulin resistance is decreased.

An additional aspect is a method of modulating the in vivo conversion of glucose to glycogen in a mammal comprising administration of an effective dose of a mildly polar extract of a plant such as *Artemisia*. Preferably, the in vivo conversion of glucose to glycogen is increased.

In another aspect, the invention provides a method of modulating the expression of insulin receptor substrate-2 (IRS-2) polypeptide in a mammal comprising administration of an effective dose of a mildly polar extract of a plant such as *Artemisia*. Preferably, the expression of IRS-2 polypeptide is increased.

A further aspect of the invention provides a method of modulating insulin-stimulated glucose uptake in a mammal comprising administration of an effective dose of a mildly polar extract of a plant such as *Artemisia*. Preferably, insulin-stimulated glucose uptake is increased.

Another aspect of the invention provides a method of modulating hepatic glucose output in a mammal comprising administration of an effective dose of a mildly polar extract of a plant such as *Artemisia*. Preferably, hepatic glucose output is decreased. It is also preferable that the extract results in a decrease in phosphoenol pyruvate carboxykinase (PEPCK) expression.

In another aspect, the invention provides a method of treating Type 2 diabetes in a mammal comprising administration of an effective dose of a mildly polar extract of a plant such as *Artemisia*.

For each of the above-described aspects of the invention drawn to methods, a preferred plant in the genus *Artemisia* is *Artemisia dracunculus*. Also, a suitable mildly polar fluid is an alcohol, with ethanol being preferred. A preferred extract lacks a detectable level of mutagen and/or no acute oral toxicity at a dosage of up to 5000 milligrams plant material per kilogram mammal body weight. An exemplary mammal to which the extracts, or pharmaceutical compositions comprising such extracts, is administered is a human. A preferred route of administration comprises nasogastric tube delivery; another preferred route of administration is oral delivery.

The present invention also discloses a method of promoting increased cellular energy in non-adipose cells, including but not limited to muscle cells and neurons, comprising administering an effective dose of a mildly polar extract of *Artemisia*, wherein the increased cellular energy provides at least one of the following advantages: increased muscle cell strength, increased muscle cell endurance, the prevention or reduction physiological distress, the prevention or reduction of fatigue, and the prevention or reduction of a nutritional deficiency.

Further disclosed is a method of preparing a mildly polar extract of a plant, such as *Artemisia*, comprising the steps of: contacting a plant such as *Artemisia dracunculus* with an elicitor and extracting the *Artemisia* with a mildly polar fluid (e.g., an alcoholic solution). As noted above, a preferred plant in the genus *Artemisia* is *Artemisia dracunculus*. Elicitors contemplated for the contacting step include those generally known in the art. Elicitors used in the contacting step include chitosan, *Trichoderma* species (preferably *Trichoderma harzianum*), acetic acid, methyl salicylate, methyl jasmonate, and PlantShield (Bioworks, Inc., Geneva, N.Y.). Suitable elicitors include 0.8 mM methyl salicylate, 0.1 mM methyl jasmonate, and PlantShield (5 to 12 ounces per 100 gallons). Preferably, the elicitor is 0.1% chitosan or *Trichoderma harzianum*. A variety of alcohols can be used to extract efficacious materials from *Artemisia*, including methanol, ethanol, and isopropanol. A preferable alcohol used to extract efficacious materials from *Artemisia* is ethanol. In yet another preferred method of preparing an alcoholic extract of *Artemisia dracunculus*, the alcoholic solution comprises at least about 60% ethanol. A preferred method of preparing the alcoholic extract further comprises disrupting the *Artemisia dracunculus*. The disrupting step can be performed by any method known in the art that results in a loss of the integrity of the plant cell wall and membrane, e.g., by grinding *Artemisia* using a mortar and pestle or a milling device. Another method of preparing the alcoholic extract further comprises drying the extract at an elevated temperature to reduce methyl eugenol concentration. Preferably, the extract comprises an effective dose of a compound selected from the group consisting of capillarisin, tetrahydroxy-methoxy flavanone, umbelliferone and its derivatives, sakuranin and its derivatives, trihydroxy-methoxy flavanone and trihydroxy flavanone.

Pharmaceutical compositions comprising a mildly polar extract of *Artemisia*, as described above, and one or more pharmaceutically acceptable formulation agents are also encompassed by the invention. The pharmaceutical compositions are used to provide therapeutically effective amounts of the mildly polar extract of *Artemisia* (e.g., *Artemisia dracunculus*) of the present invention. The invention also provides for devices to administer the extract encapsulated in a membrane.

Also encompassed by the invention are pharmaceutical compositions comprising an effective dose of a compound selected from the group consisting of capillarisin, tetrahydroxy-methoxy flavanone, umbelliferone and its derivatives, sakuranin and its derivatives, trihydroxy-methoxy flavanone and trihydroxy flavanone.

Also encompassed by the invention is the use of a pharmaceutical composition, wherein the use is selected from the group consisting of modulating glucose level in a mammal, altering the appetite of a mammal, promoting an ileal brake, modulating the binding between GLP-1 and the GLP-1 receptor, modulating alpha-glucosidase activity in a mammal, modulating insulin resistance in a mammal, modulating the in vivo conversion of glucose to glycogen in a mammal, modulating the expression of insulin-receptor substrate-2 (IRS-2) polypeptide in a mammal, modulating insulin-stimulated glucose uptake in a mammal, modulating hepatic glucose level in a mammal, treating type 2 diabetes in a mammal and promoting increased cellular energy in non-adipose cells.

The present invention contemplates a formulation for treating diabetes in a mammal comprising an *Artemisia* extract and at least one compound selected from the group consisting of gymnema sylvestre, fenugreek, bitter melon, alpha-lipoic acid, alpha-lipoic acid salts, corosolic acid, ursolic acid, D-pinitol, aloe vera, chromium picolinate, banaba leaf, yacou root, momordica charantia, olive leaf extract, pterocarpus marsupium, salacia reticulata, garlic, hawthorn, phosphatidylserine, omega 3 fatty acids, and resistant starch.

In addition, the present invention contemplates a formulation for weight control in a mammal comprising an *Artemisia* extract and at least one compound selected from the group consisting of pyruvic acid, pyruvic acid salts, L-carnitine, hydroxycitric acid, ephedrine, caffeine, conjugated linoleic acid, aspirin, alpha-lipoic acid, and alpha-lipoic acid salts.

The present invention further contemplates a formulation for promoting increased cellular energy in non-adipose cells in a mammal comprising an *Artemisia* extract and at least one compound selected from the group consisting of creatine, creatine monohydrate, a creatine salt, creatine citrate, creatine pyruvate, phosphocreatine, caffeine, alpha-lipoic acid, glucosamine, chondroitin, hydrolyzed collagen, methylsulfonyl-methane, whey protein, L-glutamine, phosphatidylcholine, choline, a choline salt, phosphatidylserine, beta-hydroxy beta-methylbutyrate, pyruvic acid, pyruvic acid salts, L-carnitine, D-ribose, a conventional or standard amino acid, a branched chain amino acid, S-adenosylmethionine, taurine, conjugated linoleic acid, alpha-lipoic acid, alpha-lipoic acid salts, and glycerin.

Numerous other aspects and advantages of the present invention will be apparent upon consideration of the following detailed description, which describes preferred embodiments of the present invention and is not meant to limit the scope of the present invention.

DETAILED DESCRIPTION OF INVENTION

Figure 1:
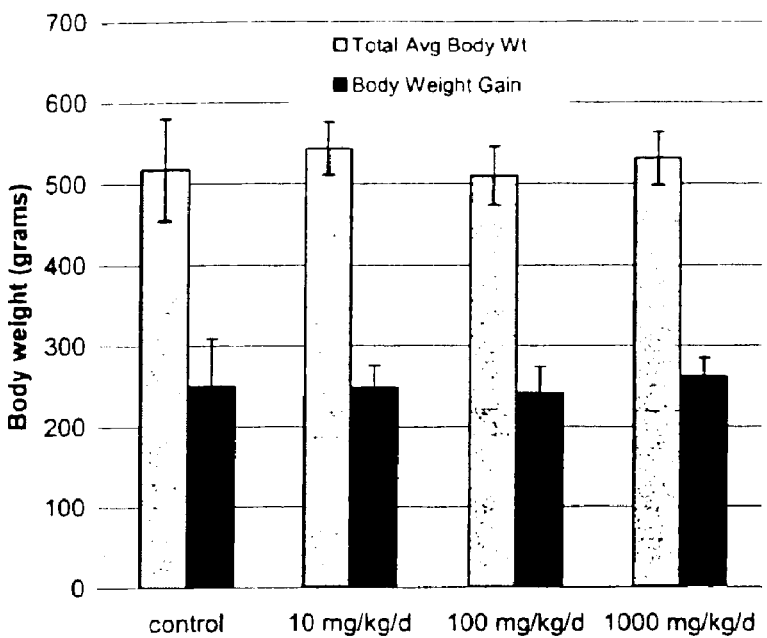
FIG. 1 presents a histogram showing weight gain and average weight for 8 to 9-week old male and female rats involved in a study of the potential long-term toxicity of *Artemisia dracunculus* extracts.
Figure 1:
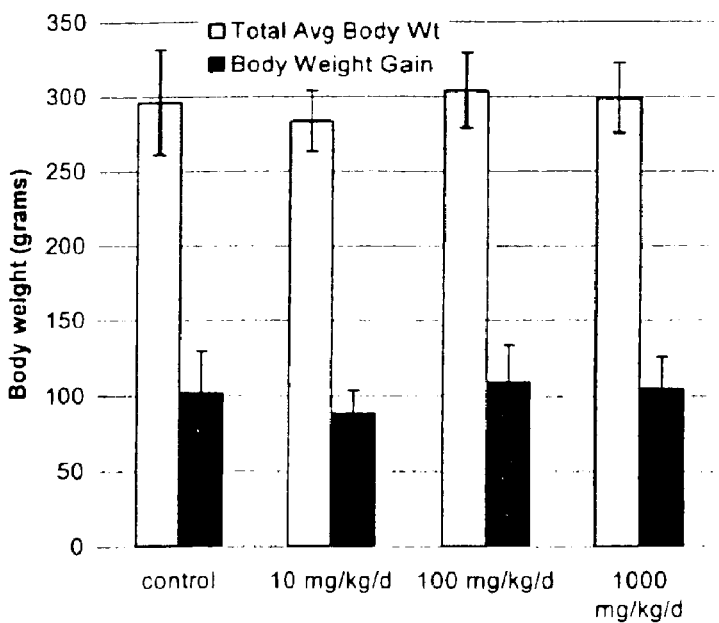

The present invention provides methods for producing (by extracting or obtaining an exudate) and recovering efficacious material from a plant such as *Artemisia*, particularly *Artemisia dracunculus*, useful in treating a variety of disease states, disorders, and conditions related to carbohydrate metabolism using a natural and inexpensive substance without the risk of unwanted side-effects. Furthermore, the efficacious material is extracted with a simple and inexpensive solvent that can readily be partially or completely removed (e.g., dried) to yield a concentrated form (e.g. powder) of the efficacious material.

The term "effective dose" as used herein means a dose comprising an extract of a plant such as *Artemisia* that is able to cause a measurable change in blood glucose levels or a measurable change in the binding affinity of GLP-1 to its native receptor. The exact value of an effective dose varies based upon the sensitivity and size of each patient, and is readily determinable by one of skill in the art using conventional procedures for the routine administration of effective dose. Preferably, the effective dose of a plant extract is between about 10 mg/kg to about 10,000 mg/kg. Preferably, the effective dose is about 1000 mg/ day.

The term "efficacious materials" as used herein refers to plant matter that is suspendable or, preferably, soluble in the extraction fluid or solution described herein such that it is administrable to mammals to elicit a beneficial physiological response. For example, administration of the efficacious material to a mammal causes a physiological response that results in a lowering of blood glucose levels.

The term "vehicle" as used herein means a carrier or diluent used in conjunction with a plant, e.g., *Artemisia*, extract which is collectively administered to a mammal. The material that serves as the vehicle is a safe material for injection or ingestion by a mammal and is generally nonmutagenic, nontoxic, and does not cause an allergic response. An example of material useful as a vehicle is physiological saline (i.e., 0.9% NaCl), 2% Tween 80 in distilled water, or a liquid or solid foodstuff.

"Mildly polar" fluid means a fluid that is slightly to moderately polar, as would be understood in the art. Mildly polar as used herein means moderately irregular distribution of electrons that is characterized by a weak to average degree of hydrophilicity. A mildly polar fluid includes all straight chain and branched primary alcohols and chemical derivatives thereof, provided that the additional chemical groups do not destroy the polarity of the fluid or increase the polarity of the fluid to the level of water, which is expressly excluded from the definition of a mildly polar fluid. Preferred mildly polar fluids are liquids, such as the lower molecular weight, straight chain, primary alcohols (e.g., ethanol). Water is not a mildly polar fluid, but is a highly polar aqueous fluid. However, a mixture of water and a mildly polar fluid (e.g., ethanol) is itself a mildly polar fluid. An example of the latter fluid is 60% ethanol.

The term "appetite of a mammal" as used herein means the capacity for nutritional intake by a mammal in relation to a reference time frame. The appetite of a mammal is measurable by simply weighing the amount of nutrition consumed by a mammal over a determined range of time. An alteration in the appetite of a mammal is determined by measuring the appetite of a treated mammal with the appetite of a similar untreated mammal over the same period of time with exposure to the same type of nutrition. Any increase or decrease in the amount of nutrition ingested by a mammal signifies an increase or a decrease in the appetite of a mammal, respectively.

"Disorders" means an undesired condition or disease of a mammal such as a human. Specifically excluded from the definition of a "disorder" or "disease" as used herein is a state of hyperlipidemia.

The protein glucagon-like peptide-1 (GLP-1) is known in the art as having multiple functions, including inhibiting gastric emptying, controlling food intake, stimulating insulin biosynthesis and secretion, inhibiting glucagon secretion, inducing islet proliferation, promoting an ileal brake, and regulating hypothalamic-pituitary function. The rate of gastric emptying, which can lead to post-prandial hyperglycemia, can be inhibited by the stimulation of an ileal brake in the distal small intestine. Among the various physiological activities of GLP-1, not all are necessarily associated with diabetes, e.g., regulation of hypothalamic-pituitary function.

The term "ileal brake" as used herein means a physiological state of the lower small intestine that interrupts the normal digestive process. Specifically, it is an endocrine-induced intestinal change in which the contents (e.g., nutrients) of the lower small intestine (ileum) influence upper gastrointestinal activity such as by decreasing gastric and pancreatic secretions and preventing gastric emptying. The extracts of the present invention, such as alcoholic extracts, may comprise efficacious materials that can cause an ileal brake.

The term "modulating" as used herein means changing, adjusting, or varying a property of an organism, tissue, cell, or molecule, including varying the quantity, activity, or capacity of a substance such as glucose or a biomolecule such as a polypeptide.

The term "extract" as used herein means a substance or composition obtained from a plant or plant part source, regardless of whether the substance or composition is found external to the plant (i.e., an exudate), is found within the plant or plant part but external to the cells thereof, or is found within the cells of the plant. Chemical and/or physical action, as would be understood in the art, may be required to obtain the substance or composition from the plant or plant part.

The term "detectable level" as used herein is the level that can be perceived using means known in the art, unless otherwise specified. For example, a detectable level of a mutagen is that level perceivable using the Ames mutagenicity test, as would be known in the art.

The term "acute oral toxicity" as used herein is given its meaning in the art of a short-term poisonous effect upon oral administration (e.g., ingestion or gavage).

Various modes of administration, including all modes known in the art, are contemplated for use in delivering the *Artemisia* extract to a mammal such as a human patient. Preferred modes of administration of the plant, e.g., *Artemisia*, extract include injection (e.g., intravenous, intramuscular and subcutaneous), inhalation, sublingual administration, oral administration, administration by nasogastric tube, rectal administration (e.g., by suppository), and topical administration. Preferably, the mode of administration is oral or by nasogastric tube.

The terms "pharmaceutically acceptable carrier" or "physiologically acceptable carrier" as used herein refer to one or more formulation materials suitable for accomplishing or facilitating the delivery of an extract of *Artemisia dracunculus* as a pharmaceutical composition.

The *Artemisia* extracts disclosed herein are extracted using a mildly polar fluid such as an alcoholic solution that does not require further fractionation, e.g., to eliminate or reduce the amount of a mutagen or toxin. This extract can be administered to mammals in an effective dose that is able to modulate blood glucose levels. Alternatively, the extract can be administered to mammals in an effective dose that is able to modulate GLP-1 activity. Other uses for the extracts of the invention include administration of a dose effective to improve nutrition, particularly sports nutrition, or to control the weight of a mammal. Moreover, the extracts of *Artemisia*, and preferably the mildly polar extracts of *Artemisia*, can be administered in combination with a wide variety of substances useful in treating, or ameliorating the symptoms of, diabetes, improving nutrition (e.g., sports nutrition) or weight control. The effective dose of *Artemisia* extract is not associated with significant mutagenic activity as determined using an Ames test, nor is it associated with a toxin. Therefore, the disclosed *Artemisia* extracts can be used to modulate blood glucose levels and modulate GLP-1 activity in an effective manner without the concerns of mutagenicity and/or toxicity.

As noted above, *Artemisia* extracts may be combined with a variety of substances in methods to treat, or ameliorate the symptoms of, diabetes. For example, an effective dose of an *Artemisia* extract may be combined with an effective dose of any one of the following naturally occurring (e.g., plant-based) substances or chemical compounds: gymnema sylvestre, fenugreek, bitter melon, alpha-lipoic acid, banaba Leaf, yacou root, momordica charantia, olive leaf extract, pterocarpus marsupium, salacia reticulate, garlic, hawthorn, corosolic acid, ursolic acid, D-pinitol, aloe vera, chromium picolinate, phosphatidylserine, omega 3 fatty acids, resistant starch, catharanthus roseus, anacardium occidentale, syzygium cumini, eucalyptus globules, lupinus albus, allium cepa, allium sativum, tecoma stans, urtica dioica, taraxacum officinale, kyllinga monocephala, phyllanthus emblica, phyllanthus niruri, azadirachta indica, morbus alba, poterium ancistroides, and daucus carota. These combinations of substances for use in methods for treating, or ameliorating the symptoms of, diabetes provide the benefits attributable to each component (i.e., the *Artemisia* extract and the substance with which it is combined for administration).

Also as noted above, *Artemisia* extracts may be combined with a variety of substances in methods of improving nutrition, such as sports nutrition. In such methods, an effective dose of an *Artemisia* extract is combined with an effective dose of any one of the following naturally occurring (e.g., plant-based) substances or chemical compounds: creatine, creatine monohydrate, creatine salts such as creatine citrate, creatine pyruvate, creatine derivatives and salts thereof, phosphocreatine, caffeine, alpha-lipoic acid, glucosamine, chondroitin, hydrolyzed collagen, methylsulfonyl-methane, whey protein, L-glutamine, phosphatidylcholine, choline, choline salts, phosphatidylserine, beta-hydroxy beta-methylbutyrate, pyruvate, L-carnitine, D-ribose, an amino acid (a conventional amino acid), a branched chain amino acid, S-adenosylmethionine, taurine, conjugated linoleic acid, alpha-lipoic acid, alpha-lipoic acid salts, and glycerin. In referencing the salts of various compounds, the invention contemplates the compound and any suitable salt-forming counterions (such as alkali metal ions, alkaline earth metal ions, halogen ions, organic cations, organic ions, complex ions and any other counterion known in the art (preferably sodium)). These combinations of substances for use in methods for improving nutrition, such as sports nutrition, also provide the benefits attributable to each component (i.e., the *Artemisia* extract and the substance with which it is combined for administration).

Further, as noted above, *Artemisia* extracts may be combined with a variety of substances in methods for weight control. In such methods, an effective dose of an *Artemisia* extract is combined with an effective dose of any one of the following naturally occurring (e.g., plant-based) substances or chemical compounds: pyruvate, L-carnitine, hydroxycitric acid, ephedrine, caffeine, and conjugated linoleic acid (CLA). These combinations of substances for use in methods for improving nutrition, such as sports nutrition, also provide the benefits attributable to each component (i.e., the *Artemisia* extract and the substance with which it is combined for administration). Although the same combination of substances may be useful in more than one method, the methods are nonetheless distinguishable based on purpose.

The following examples illustrate embodiments of the invention. Example 1 describes the preparation of an extract of *Artemisia dracunculus*. Example 2 discloses the efficacy of alcoholic extracts of *Artemisia dracunculus*. Example 3 describes the hypoglycemic activity of alcoholic extracts on non-diabetic mice. Example 4 discloses the effect of alcoholic extracts on carbohydrate metabolism using rat epididymal adipose tissue. Example 5 shows the effect of alcoholic extracts on proteins involved in carbohydrate metabolism. Example 6 describes the toxicology of *Artemisia dracunculus* extract. Example 7 shows the effect of *Artemisia dracunculus* extract on insulin-stimulated glucose uptake. Example 8 discloses the effect of *Artemisia dracunculus* extract on PEPCK expression and hepatic glucose output. Example 9 discusses the amount of estragole and methyl eugenol in an *Artemisia dracunculus* extract. Example 10 describes *Artemisia dracunculus* cultivation. Example 11 discloses the process of extracting and storing *Artemisia dracunculus* extract. Example 12 describes the liquid chromatography-mass spectrometry (LC-MS) and gas chromatography-mass spectrometry (GC-MS) analyses of an *Artemisia dracunculus* extract. Example 13 discusses *Artemisia dracunculus* extract compositions and administration.

EXAMPLE 1

Extract Preparation

*Artemisia dracunculus* seeds (Richters Seeds) were germinated in a 0.9 cm deep well inside Grodan rock wool cubes (3.4 cm width×3.4 cm depth×3.7 cm height). One week later the seedlings were placed into a hydroponic system with a nutrient solution (120 g Hydro-Sol [Scotts-Sierra Horticultural Products Comp., Marysville, Ohio, USA] supplemented with 5 g $NH_4NO_3$ and 90 g $Ca(NO_3)_2$ in 60 liters of water). Aeration was provided by bubbling compressed air through the hydroponic nutrient solution at a flow rate of about 100 ml per minute for deep hydroponics (i.e., continuous immersion in water deeper than 4 cm). Alternatively, the seedlings were placed into a shallow gutter hydroponic system with a continuous flow of nutrient solution. The plants were elicited with 0.1% chitosan in the hydroponic solution 24 hours prior to harvest. The use of chitosan for elicitation of the plants provided greater hypoglycemic (i.e., blood glucose lowering) activity than untreated plants or plants treated with other elicitors, such as acetic acid, salicylic acid, and methyl jasmonate.

The entire plant above the root crown was harvested and freeze-dried after 4 to 6 weeks of growth. The dried plant material was then ground to a fine powder in a laboratory mill with a 2 mm mesh screen and extracted with a 60% ethanol solution. For the initial extraction, a solvent mass 10 times greater than the mass of the powdered *Artemisia* was used. The mixture was heated to 70° C. for 1 to 4 hours. The solid portion was removed by centrifugation and rinsed with an amount of 60% ethanol equal to 2–4 times the approximate mass of the pellet. The pellet rinsing was repeated 3 times. The ethanol was then removed from the solution in vacuo with a rotor evaporator to a volume of less than 50% of the starting volume. The remaining water was removed by freeze-drying. The greenish powder remaining after freeze-drying was one form of an *Artemisia dracunculus* extract.

EXAMPLE 2

Efficacy of Alcoholic Extract of *Artemisia dracunculus*

The efficacy of the *Artemisia dracunculus* extract was evaluated in Streptozotocin (STZ)-treated mice. STZ induces diabetes by destroying most, if not all, of the beta cells of the pancreas, leaving the animals with little or no insulin production and severe hyperglycemia [Hisashi, et al., *European Journal of Pharmacology*, 87:237–243 (1983)]. This is a stringent assay for anti-diabetic efficacy, in which many of the currently prescribed drugs do not show significant activity. Mice were treated with STZ as described by Hisashi et al., *European Journal of Pharmacology*, 87:237–243 (1983). A 500 mg/kg dose of *Artemisia dracunculus* extract was administered daily by oral gavage to STZ-treated mice for a period of 7 days. Additionally, a dose of insulin (1 IU/kg) was administered. subcutaneously to STZ-treated mice, while 20 ml/kg of vehicle only (0.9% NaCl or 2% Tween 80 in distilled water) was administered to STZ-treated mice, as a control. The *Artemisia dracunculus* extract-treated mice showed a decrease in blood glucose concentrations of about 20%, which is about half the activity produced by injected insulin (42% reduction). Without wishing to be bound by theory, it would appear that, because *Artemisia dracunculus* extract is active in insulin-deficient animals, it is likely that its mode of action does not involve the stimulation of insulin production. Regardless of mechanism, however, the results establish that plant extracts, such as the mildly polar ethanolic extract of *A. dracunculus*, can be orally administered in a dose effective in lowering blood glucose levels. In addition, these results establish the efficacy of the plant extracts of the invention in treating either Type 1 or Type 2 diabetes, or ameliorating symptoms thereof.

KK-A$^y$ Diabetic Mice

*Artemisia dracunculus* extract was also evaluated as an anti-diabetic in KK-A$^y$ genetically diabetic mice, a reliable and predictive in vivo model of diabetes useful in treatment screens. KK-A$^y$ mice develop severe diabetes naturally as they mature and have high blood glucose concentrations as a result of insulin resistance [Suto et al., *Euro. J. Endocrin.,* 139:654–661 (1988); Shimura et al., *Biol. Pharm. Bull.* (1997)]. These mice also have very high blood insulin concentrations that are ineffective in lowering blood glucose. Mature KK-A$^y$ mice were exposed to *Artemisia dracunculus* extracts prepared as described in Example 1. The extract was administered to the mice by oral gavage. To obtain reliable data, control mice were provided with vehicle only by oral gavage. For comparative purposes, some mice were treated with either of two known hypoglycemic drugs (Troglitazone or Metformin). The feeding regimen was continued for seven days, and insulin and blood glucose levels were then determined using conventional techniques known in the art, i.e., a glucose HA assay using a Glucose HA Assay kit (Wako, Japan) and ELISA insulin assays using an ELISA Insulin Assay kit (SPI bio, France).

Table 1, below, shows results obtained from KK-A$^y$ mice. The *Artemisia dracunculus* extract significantly reduced blood glucose concentrations in the KK-A$^y$ mice, with efficacy similar to hypoglycemic drugs, as shown in Table 1. An unpaired Students t test was applied for comparison between the vehicle and test groups and significance at a level of $P<0.01$ was calculated. Troglitazone, used as the reference drug for this assay because of its effectiveness in lowering blood glucose, currently is not on the market because of hepatotoxicity [Physicians Desk Reference, PDR, Electronic Library, Medical Economics Group, Inc., Montvale, N.J. (2001)]. Metformin is an efficacious drug with a long history of use, but has many well-documented side effects [PDR, 2001]. In addition to lowering blood glucose concentrations, *Artemisia dracunculus* extracts induced a reduction in the elevated blood insulin levels of KK-A y mice, similar to the oral hypoglycemic drugs. Again without wishing to be bound by theory, these results suggest potentially similar modes of action for *Artemisia dracunculus* extracts and these drugs, which involve an increase in insulin sensitivity rather than concentration.

TABLE 1

Activity of *Artemisia dracunculus* extract and Synthetic Anti-Diabetic Drugs in Genetically Diabetic KK-A$^y$ Mice after 7 Days of Feeding.

| Treatment | Oral Dose | Insulin Reduction | Blood Glucose Reduction |
|---|---|---|---|
| Vehicle | 10 ml/kg | — | — |
| Artemisia dracunculus extract | 500 mg/kg | 33% | 24% |
| Troglitazone | 30 mg/kg | 48% | 30% |
| Metformin | 300 mg/kg | 52% | 41% |

Toxicity

The literature related to *Artemisia* suggests toxicity concerns attend the intake of *Artemisia*. To assess the potential acute oral toxicity of *Artemisia dracunculus* alcoholic extracts, feeding studies using the alcoholic extracts were performed on rats.

The alcoholic extract was administered to ten healthy rats by oral gavage in the amount of 5,000 mg/kg of body weight. The animals were observed for mortality, signs of gross toxicity, and behavioral changes at least once daily for 14 days. All animals survived, gained weight and appeared active and healthy. Also, gross necropsy on the subject rats at terminal sacrifice was unremarkable. The results show that *Artemisia dracunculus* extracts had no acute oral toxicity at 5000 mg/kg, the maximum dosage mandated for testing under applicable FDA regulations.

Mutagenicity

Another major concern with plant extracts is that such preparations often contain mutagens, as revealed by a positive response using a standard Ames test for mutagenicity. See Ames et al., *Mutation Res.,* 31:347 (1975). A "positive response" as used in the context of the Ames mutagenicity test, is more readily understood with an appreciation of the Ames test. The Ames test subjects a collection of five HIS$^-$ *Salmonella typhimurium* strains to potential mutagens and selects for reversion to HIS$^+$. In addition to being HIS$^-$, these five strains have been engineered to be more sensitive to mutagens. A positive response in the Ames test is a detectable increase in the frequency of reversion to HIS$^+$ relative to controls (i.e., same strain(s) not subjected to the potential mutagen). Each strain is examined both with and without metabolic activation in order to account for those mutagens that are only active in vivo, as metabolic derivatives. Complete mutagenic testing of alcoholic *Artemisia dracunculus* extracts with the Ames test was performed. The results of the Ames test showed that *Artemisia dracunculus* extracts did not induce any detectable mutagenic effects, either with or without metabolic activation, and was therefore considered non-mutagenic using the industry-standard Ames mutagenicity test.

The efficacy and toxicity evaluations were performed by MDS Pharma Services Co., (11804 North Creek Parkway, South Bothell, Wash. 98011), a pharmacological testing company. The oral acute toxicity testing was performed by PSL (Product Safety Laboratory, 725 Cranbury Road, East Brunswick, N.J.), a division of ENi Laboratories Inc., 2394 Route 130 Dayton, N.J. 08810. All of these studies complied with good laboratory practices as defined in 21 C.F.R. §58; U.S. FDA Good Laboratory Practice Standards; OECD (Organization for Economic Co-operation and Development) Principles of Good Laboratory Practice C(97) 186/Final; and in accordance with Health Effects Test Guidelines, OPPTS 870.1100 (1998). The protocols used by MDS Pharma Services Co. and PSL are described herein.

EXAMPLE 3

Hypoglycemic Activity of Alcoholic Extract on Non-Diabetic Mice

The possible hypoglycemic activity of *Artemisia dracunculus* extracts was investigated in non-diabetic mice. The mice were exposed to *Artemisia dracunculus* extracts prepared as described in Example 1, which were administered orally to the mice in the form of a coating on their food. To obtain reliable data, control mice were provided with vehicle-coated food. The vehicle was 0.9% NaCl or 2% Tween 80 in distilled water. The feeding regimen was continued for seven days, and insulin and blood glucose levels were then determined using a technique well known in the art. (ELISA Insulin Assay kit (SPI bio, France); Glucose-HA Assay kit (Wako, Japan)). Mice fed vehicle (10 ml/kg) served as the control. *Artemisia dracunculus* extracts, at a dosage level of 500 mg/kg, caused statistically insignificant reductions in the blood glucose concentrations of non-diabetic animals, the changes in insulin concentrations of the extract-fed mice were nearly identical to that of the controls, and the blood glucose levels were reduced 18% more in the extract-fed mice than in the controls. An unpaired Students t test was applied for comparison between the vehicle and test group and significance at a level of $P<0.05$ was not achieved, signifying that the decrease was not significant. Thus, the methods of the invention may be used to treat human, or non-human, mammals without grave concern that only diabetics receive treatment. The methods are well-suited, e.g., for treatment of groups of mammals, such as herds of cattle, sheep or pigs.

EXAMPLE 4

Effect of Alcoholic Extract on Carbohydrate Metabolism

A cellular glucose uptake assay was used to determine if the *Artemisia* extract directly influenced the somatic uptake of glucose from the blood as a means of correcting hyperglycemia. In this assay, isolated rat epididymal adipose tissue was used as a model of glucose metabolism that is very sensitive to insulin stimulation of glucose uptake [Rodbell, *J. Biol. Chem.*, 239:375 (1964)] and was performed by MDS Pharma Services using a standard and well-known protocol. Epididymal fat from male rats was minced and degraded in a solution containing radiolabelled 0.1 mM glucose. Incorporation of radioactive D-[3-$^3$H] glucose (0.05 µCi) into lipids from the tissue was measured by scintillation counting to provide an index of insulin-stimulated glucose metabolism. An increase of intracellular glucose of greater than 50% in the presence of the test substance relative to the insulin response was used as an indication that the test substance increased insulin receptor agonist activity. Inhibition of insulin-induced glucose incorporation by the test substance of greater than 50% indicated that the test substance decreased insulin receptor activity. Many of the currently used prescription drugs, including Metformin and Glibenclamide, influence glucose uptake by cells. The influence of *Artemisia dracunculus* extracts on glucose uptake by fat cells over a wide concentration range is shown in Table 2.

TABLE 2

Activity of *Artemisia dracunculus* extract in the cellular glucose uptake assay with rat epididymal adipose tissue

| Glucose Concentration | Increase (%) | Decrease (%) |
|---|---|---|
| 1000 µg/ml | −14 | −12 |
| 100 µg/ml | −8 | −9 |
| 10 µg/ml | −2 | −5 |
| 1 µg/ml | −5 | 17 |
| 0.1 µg/ml | −3 | 10 |

*Artemisia dracunculus* extracts did not promote or inhibit glucose uptake in adipose tissue (% increases and % decreases of glucose uptake were not significant over a wide range of glucose concentrations), suggesting that the mode of action of the *Artemisia dracunculus* extract does not involve the stimulation of glucose uptake into fat cells. This is in marked contrast to the effect that these extracts have on glucose uptake by other cell types, e.g., muscle cells and neurons (discussed in Example 7). These findings also indicate that *Artemisia* extract may modulate blood glucose levels in diabetics without causing weight gain.

EXAMPLE 5

Effect of Alcoholic Extract on Proteins Involved in Carbohydrate Metabolism

GLP-1, a protein involved in carbohydrate metabolism, has multiple functions, including enhancement of insulin secretion, stimulation of proinsulin gene expression, and suppression of glucagon secretion and gastric emptying [(Drucker, *Diabetes*, 47:159–169 (1998); Fehmann et al., *Endocr. Rev.*, 16:390–410 (1995)]. GLP-1 may also increase insulin sensitivity as well as stimulate pancreatic β-cell proliferation [(Sandhu et al., *Diabetes*, 48: 1045–1053 (1999); Wang et al., *Endocrinology*, 140: 4904–4907 (1999)].

In vitro assays were performed to measure the following: 1) intestinal brush border α-glucosidase enzyme activity; 2) the binding of human glucagon-like peptide-1 (GLP-1) to its receptor; and 3) the binding of insulin to its receptor, in order to assess whether the extracts affected enzyme activity and/or hormone-receptor binding. The results are shown below in Table 3.

Some drugs for the treatment of diabetes, such as acarbose, precose and glycet, reportedly inhibit the intestinal brush border α-glucosidase enzyme responsible for the release of glucose from sucrose and starches [Luna et al., *American Family Physician* 63(9):1747–56 (2001)]. The hydrolysis of complex carbohydrates by α-glucosidase leads to postprandial hyperglycemia in the diabetic patient. *Artemisia dracunculus* extracts were evaluated as a potential α-glucosidase inhibitor using a standard assay for drug discovery involving a rice-derived α-glucosidase [Pillar et al., *Biochimica Biophysica Acta* 1292:197–205 (1996)].

The α-glucosidase enzyme was incubated with the extract (experimental condition), or without the extract (control), and p-nitrophenyl α-D-glucopyranoside for 90 minutes in MES buffer, pH 6.3, at 70° C. The reaction was stopped with 1 M sodium carbonate and absorbance was determined spectrophotometrically at 405 nm. The change in absorbance was proportional to the release of p-nitrophenol, which was used to calculate the percent increase or decrease in α-glucosidase activity ascribable to the extract.

*Artemisia dracunculus* extracts did not inhibit α-glucosidase activity, as shown in Table 3 (the negative percent inhibition indicates stimulation or activation), but rather promoted an increase in activity in a dose-dependent manner. Therefore, the altered level of α-glucosidase activity does not explain the hypoglycemic effect of *Artemisia dracunculus* extracts. Without wishing to be bound by theory, this result suggests that the *Artemisia dracunculus* alcoholic extract may influence other aspects of glucose metabolism.

*Artemisia dracunculus* extracts were found to significantly affect the binding of human glucagon-like peptide-1 (GLP-1) to its receptor (as shown in Table 3). Membranes from cells stably transfected with a plasmid encoding the human GLP-1 receptor were incubated with [$^{125}$I]GLP-1 (7–36), amide (2000 Ci/mmol; Amersham Biosciences, Piscataway, N.J.) for 90 minutes at 37° C. The membranes were then washed and counted for radioactivity to determine the amount of [$^{125}$I]GLP-1 (7–36), amide specifically bound. The relative percent increase or decrease in binding due to the presence of the extract was calculated.

The results of the assay of GLP-1 binding showed that the negative inhibition or enhancement of GLP-1 binding was significant and dose-dependent. Thus, the *Artemisia dracunculus* extract increased GLP-1 binding to its receptor (as shown in Table 3), including activity implicated in diabetes. This result suggests that one way that an *Artemisia dracunculus* alcoholic extract affects glucose metabolism in diabetics may be by increasing GLP-1 binding to its receptor.

Similarly, the ability of *A. dracunculus* extracts to interfere directly with insulin binding to its receptor was measured (as shown in Table 3) to determine if the extract has an insulinomimetic or insulin-potentiating activity. An insulin binding assay was used to evaluate the ability of test compounds to compete with the binding of insulin to its receptor. A standard insulin binding assay currently used for drug discovery and insulin stability testing, described in Koch et al., *Hoppe-Seyler's Z. Physiol. Chem.* 362:S.347–351 (1981), was used.

Insulin binding assays were performed, as described in Koch et al., using the *Artemisia dracunculus* extracts. Liver membranes from male rats were incubated with [$^{125}$I] insulin for 16 hours at 4° C. The membranes were then washed and counted for radioactivity to determine the amount of [$^{125}$I] insulin that was specifically bound. The ability of the extract to increase or decrease the binding of insulin to the receptor (membranes) was then calculated.

*Artemisia dracunculus* extracts had no significant effect on the binding of insulin to its receptor in this assay. This result suggests that the *Artemisia dracunculus* alcoholic extract may not exert its effect by influencing insulin binding.

TABLE 3

In vitro activity of *Artemisia dracunculus* extract in enzyme inhibition and binding assays

| Assay | Concentration | % Inhibition |
| --- | --- | --- |
| α-D-glucosidase | 1000 μg/ml | −109 |
| α-D-glucosidase | 100 μg/ml | −62 |
| GLP-1 Binding | 1000 μg/ml | −74 |
| GLP-1 Binding | 100 μg/ml | −45 |
| Insulin Binding | 1000 μg/ml | 5 |

Thus, another aspect of the invention is drawn to methods of modulating GLP-1 activity. Preferably, the modulation is a stimulatory change. These methods are useful in treating diabetes, particularly Type 2 diabetes, or at least one symptom associated with such diseases or disorders. Preferably, the methods achieve this beneficial effect without reducing or avoiding GLP-1-induced postprandial hyperglycemia. A related aspect of the invention is a modulator of GLP-1 activity comprising a plant extract according to the invention, such as an *Artemisia dracunculus* extract.

EXAMPLE 6

Toxicology of the Extracts

A 90-day chronic toxicity study was carried out in eight- to nine-week-old male and female rats with the *Artemisia dracunculus* extract. No visible signs of toxicity were observed in any of the animals regardless of the treatment concentration. Gross necropsies were performed, blood samples collected, and tissue samples were subjected to histological evaluation. There were no apparent differences in the body weight gain of any of the treated rats compared to the non-treated rats (see FIG. 1). There were also no apparent differences in blood glucose or insulin concentrations between the treated and control rats. Without wishing to be bound by theory, *Artemisia dracunculus* extract does not appear to significantly alter body weight or blood glucose and insulin concentrations. Accordingly, it is expected that histological examinations will confirm the absence of detectable toxicity in the extracts of the invention. These findings confirm the observations based on the data presented in Example 4, which indicates that *Artemisia* extract modulates blood glucose levels in diabetics without causing weight gain.

EXAMPLE 7

Effect of *Artemisia dracunculus* on Insulin-Stimulated Glucose Uptake

Figure 2:
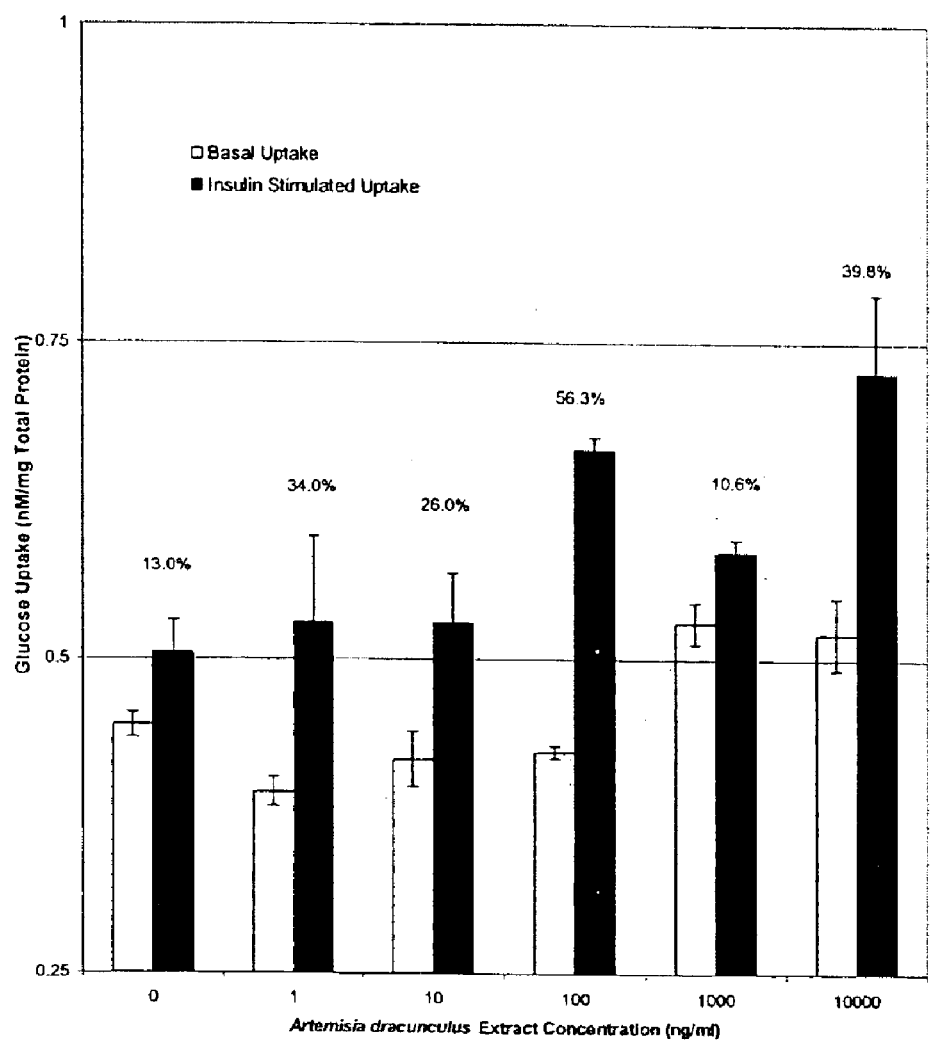
FIG. 2 presents a histogram showing the effect of *Artemisia dracunculus* extracts on insulin-stimulated glucose uptake in primary skeletal muscle cell cultures from obese Zucker rats.

Skeletal muscle cells serve as the major site of insulin-stimulated whole body glucose disposal. The efficiency of glucose uptake by muscle cells under conditions of insulin stimulation is diminished by the development of insulin resistance associated with Type 2 diabetes. The potential ability of *Artemisia dracunculus* extract to have a favorable effect on carbohydrate metabolism was assessed by measuring basal and insulin-stimulated glucose uptake in primary skeletal muscle cell cultures. Specifically, muscle cells were taken from an insulin-resistant animal model, i.e., the obese Zucker rat, and grown in tissue culture. After cells were grown to approximately 75% confluence, the cells were incubated with *Artemisia dracunculus* extract over a wide range of concentrations (0–10,000 ng/ml; see FIG. 2). Glucose uptake [nM glucose/mg muscle protein (as determined by the Bradford protein assay)] was then measured under basal conditions (no insulin) or after insulin stimulation (100 nM). The numbers above the bars in the histogram indicate the percent increase in glucose uptake over the corresponding non-insulin treated cells. The highest concentration of *Artemisia dracunculus* extract was associated with up to a 40% increase in insulin-stimulated glucose uptake as compared to the non-treated controls, and this effect appears to be dose-dependent. The extract did not have significant effects in the absence of insulin (basal conditions). Therefore, *Artemisia dracunculus* extract appears to increase the effectiveness of insulin-stimulated glucose uptake by decreasing insulin resistance.

Figure 3:
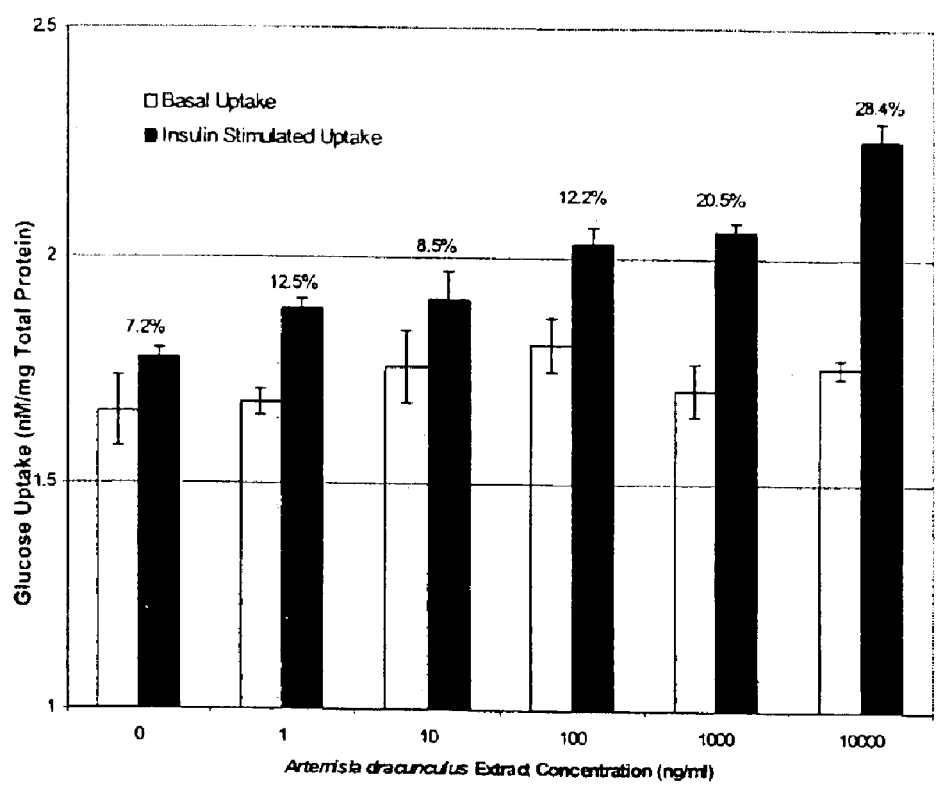
FIG. 3 presents a histogram showing the effect of *Artemisia dracunculus* extracts on insulin-stimulated glucose uptake in human skeletal muscle cell cultures.

This assay was also performed with human skeletal muscle cell cultures and can be used to determine effective human doses because the art recognizes that the in vitro system is predictive of the in vivo system (Henry et al., 1995). As with the Obese Zucker rat cultures, *Artemisia dracunculus* extract significantly increased insulin-stimulated glucose uptake in human skeletal muscle cells in a dose-dependent manner (see FIG. 3). The total increase in insulin-stimulated glucose uptake was lower in the human skeletal muscle cells than in the obese rat cells. The human skeletal muscle cells were not of diabetic or obese origin, however, and are metabolically distinct from cells that are of obese origin or insulin-resistant. *Artemisia dracunculus* extract did not promote glucose uptake in the absence of insulin and is, therefore, not likely to have any hypoglycemic effects.

The insulin response is complex and involves receptor binding, a multitude of intracellular cascades, the translocation of glucose transporters, and the conversion of transported glucose into glycogen. In addition to the uptake of glucose, studies in skeletal muscle cell cultures showed that *Artemisia dracunculus* extract increases the conversion of glucose into glycogen, thereby supporting a sustained decrease in insulin resistance (data not shown).

Figure 4:
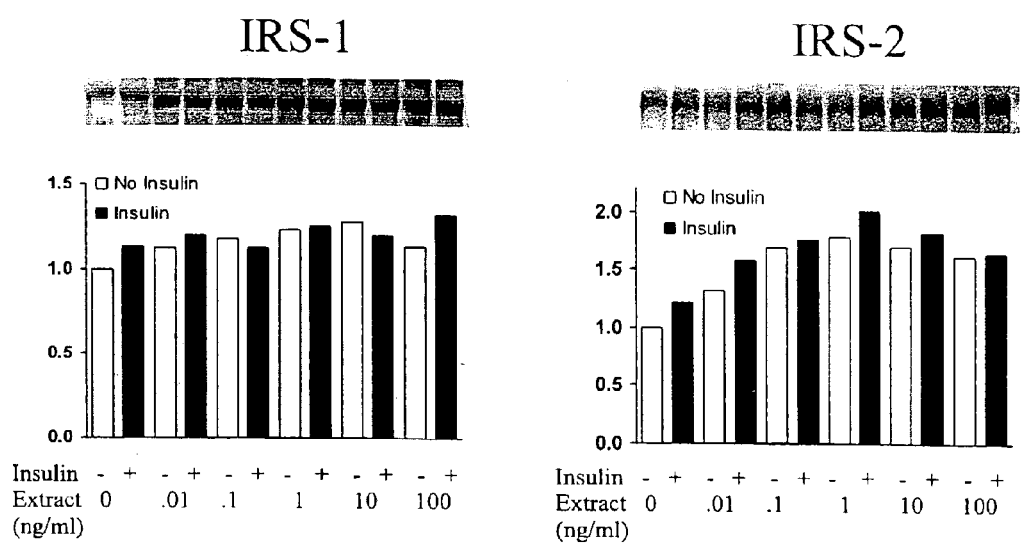
FIG. 4 shows the Insulin-Receptor Substrate 1 (IRS-1) and Insulin-Receptor Substrate 2 (IRS-2) protein content in human skeletal muscle cell cultures treated with insulin and *Artemisia dracunculus* extract.

Insulin receptor substrates (IRS-1 and IRS-2) are key messengers in this insulin-signaling cascade. Therefore, concentrations of these important proteins were quantified after treatment with *Artemisia dracunculus* using Western blot analysis with anti-IRS-1 and anti-IRS-2 antibodies and densitometry. IRS-1 and IRS-2 were measured in human skeletal muscle cells in response to treatment with *Artemisia dracunculus* extract over a range of concentrations (0–100 ng/mL) both with and without insulin (see FIG. 4). There was a significant increase in the IRS-2 protein level after treatment with *Artemisia dracunculus* extract.

Without wishing to be bound by theory, *Artemisia dracunculus* extract does not appear to have any hypoglycemic effects. However, there is evidence to suggest that *Artemisia dracunculus* extract may lower insulin resistance and increase IRS-2 protein expression.

Accordingly, mildly polar extracts of plants such as members of the *Artemisia* genus (e.g., *dracunculus*) are useful in treating diabetes, or ameliorating at least one symptom associated therewith. In particular, such extracts are useful in lowering blood glucose levels, particularly of Type 2 diabetics. Preferred extracts of the invention lower the insulin resistance associated with Type 2 diabetes. Preferred extracts of the invention increase IRS-2 expression. Moreover, these beneficial uses of the extracts may be realized without narrowly tailoring the method to diabetics (e.g., Type 2 diabetics) because the extracts do not appear to induce cellular glucose uptake independent of insulin.

EXAMPLE 8

Effect of *Artemisia dracunculus* on PEPCK Expression and Hepatic Glucose Output

*Artemisia dracunculus* extract is a complex mixture potentially containing several compounds with activity related to the regulation of blood glucose concentrations. One of the major contributors to hyperglycemia in diabetic patients is an elevated hepatic glucose output due to the absence or ineffectiveness of insulin as a signal to decrease the hepatic glucose output as occurs in non-diabetics. In order to determine the effect of *Artemisia dracunculus* extract on hepatic glucose output as a potential mode of action, PEPCK mRNA expression was measured as an indicator of hepatic glucose output in *Artemisia dracunculus* extract-treated STZ-diabetic rats and their non-diabetic controls as shown in Table 4. PEPCK is a key enzyme of gluconeogenesis, a primary metabolic pathway leading to the production and release of glucose in the liver. PEPCK mRNA expression is greatly elevated in diabetic animals, but was significantly reduced in diabetic animals treated with *Artemisia dracunculus* extract. *Artemisia dracunculus* extract did not affect PEPCK-mRNA expression in non-diabetic animals and appears to be specific to the diabetic state (see Table 4).

TABLE 4

The Effect of *Artemisia dracunculus* extract on PEPCK mRNA expression in rat liver.

| Animal | Treatment | PEPCK mRNA abundance |
| --- | --- | --- |
| STZ diabetic rats | *Artemisia dracunculus* extract | *10643 +/- 177 |
|  | Vehicle | *14731 +/- 1722 |
| Control rats | *Artemisia dracunculus* extract | 4468 +/- 729 |
|  | Vehicle | 4421 +/- 797 |

Results are given as the mean +/- SEM of 5 animals, *considered significant at $P < 0.05$ Without wishing to be bound by theory, *Artemisia dracunculus* appears to inhibit PEPCK mRNA expression in diabetics, thus decreasing hepatic glucose output. *Artemisia dracunculus* may also decrease hepatic glucose output by other means as well.

Thus, another aspect of the invention is a method of decreasing (e.g., inhibiting) PEPCK expression in diabetic organisms. Preferred extracts lower the expression of PEPCK specifically in mammals exhibiting symptoms of diabetes.

EXAMPLE 9

Estragole and Methyl Eugenol in *Artemisia dracunculus* Extract

Estragole and methyl eugenol are common constituents of herbs and their essential oils. Estragole is especially common in the essential oil of tarragon and is the compound responsible for the anise-like taste of tarragon. Since 1965, estragole has been generally recognized as safe but is currently considered genotoxic and carcinogenic by the European Scientific Committee on Food. The estragole content of *Artemisia dracunculus* extract was determined to be below the limits of detection by gas chromatography-mass spectrometry (GC-MS) (below 0.001%). *Artemisia dracunculus* does contain estragole, but estragole is a volatile compound that is removed during the preparation of *Artemisia dracunculus* extracts. Methyl eugenol is also considered to be genotoxic and carcinogenic but is a common dietary component and is found in very high concentrations in basil and other herbs. Methyl eugenol was detected in *Artemisia dracunculus* extract and its concentration was determined to be less than 0.17%. Drying the extract at elevated temperatures reduced the methyl eugenol content of the extract by an additional 40-fold. Dietary sources of methyl eugenol were estimated to contribute to an intake of 0.19–0.53 mg/kg of body weight per day. The amount of methyl eugenol from *Artemisia dracunculus* extract based on a predicted daily intake of 1000 mg/day would therefore be 0.02 mg/kg of body weight per day. Therefore, the methyl eugenol of *Artemisia dracunculus* extract received by an individual would be far less than received from other dietary sources. Thus, the content of estragole and methyl eugenol in *Artemisia dracunculus* extracts is relatively insignificant, because they are either non-existent (estragole) or present at very low levels (methyl eugenol).

Thus, these studies further establish the safety of the materials and methods of the invention. Those compounds of questionable safety (e.g., estragole and methyl eugenol) have been shown to be absent or present at insignificant levels in the preferred extracts of *A. dracunculus*.

EXAMPLE 10

*Artemisia dracunculus* Cultivation

The preceding examples have established the efficacy and safety of the materials and methods of the invention. Other advantages of the present invention include the low cost and ease of generating the source plant materials. Large-scale cultivation of *Artemisia dracunculus* can be accomplished in a continuous flow commercial hydroponic greenhouse. A natural preparation of *Trichoderma harzianum* was added to the hydroponic medium to prevent disease and to serve as an elicitor. *Trichoderma* is a beneficial microbe that stimulates the defense system of plants. Liquid chromatography-mass spectrometry (LC-MS) biochemical profiles were used to confirm that the plants grown in the research greenhouse were analogous to those grown commercially.

Compound Separation and Analysis

Preparative. The extract was dissolved in 60% ethanol and subjected to preparative HPLC separation and fractionation. Waters (Milford, Mass.) HPLC equipment was used, including W600 preparative pump with W600 pump controller, W717plus auto-sampler with 2.5 ml syringe, W490E programmable multi-wavelength detector with preparative flow cell. Data were collected and stored using the Waters'Millennium v. 2.10 software. Extracts were separated on a 300×19 mm Waters SymmetryPrep™ reverse phase C-8 column, particle size 7 μm, equipped with Waters Guard-Pak™ pre-column. The mobile phase consisted of 2 components: 0.5% ACS grade acetic acid in double distilled de-ionized water, pH 3–3.5 (solvent A), and Acetonitrile (solvent B). The mobile phase flow was adjusted at 8.0 ml/min, and generally a gradient mode was used for all initial separations, as follows: 0–35 min 95% A –5% A; 35–40 min 5% A; 40–45 min 5% A–95% A.

Analytical. Individual fractions were dissolved in 60% ethanol and analyzed with the Waters (Milford, Mass.) LC-MS Integrity™ system consisting of a solvent delivery system including a W616 pump and W600S controller, W717plus auto-sampler, W996 PDA detector and Waters TMD Thermabeam™ electron impact mass detector. Data were collected & analyzed with the Waters Millennium® v. 3.2 software, linked with the 6th edition of the Wiley Registry of Mass Spectral Data, containing 229,119 spectra of 200,500 compounds. Substances were separated on a Phenomenex® Luna C-8 reverse phase column, size 150×2 mm, particle size 3 $\mu$m, pore size 100 Å, equipped with a Phenomenex® SecurityGuard™ pre-column. The mobile phase consisted of 2 components: Solvent A (0.5% ACS grade acetic acid in double-distilled de-ionized water, pH 3–3.5), and Solvent B (100% Acetonitrile). The mobile phase flow was adjusted at 0.25 ml/min, and generally a gradient mode was used for all analyses. To maximize reproducibility between the preparative and the analytical systems, identical gradient profiles were used for the LC-MS analyses, although the retention times of each system did differ.

Figure 5:
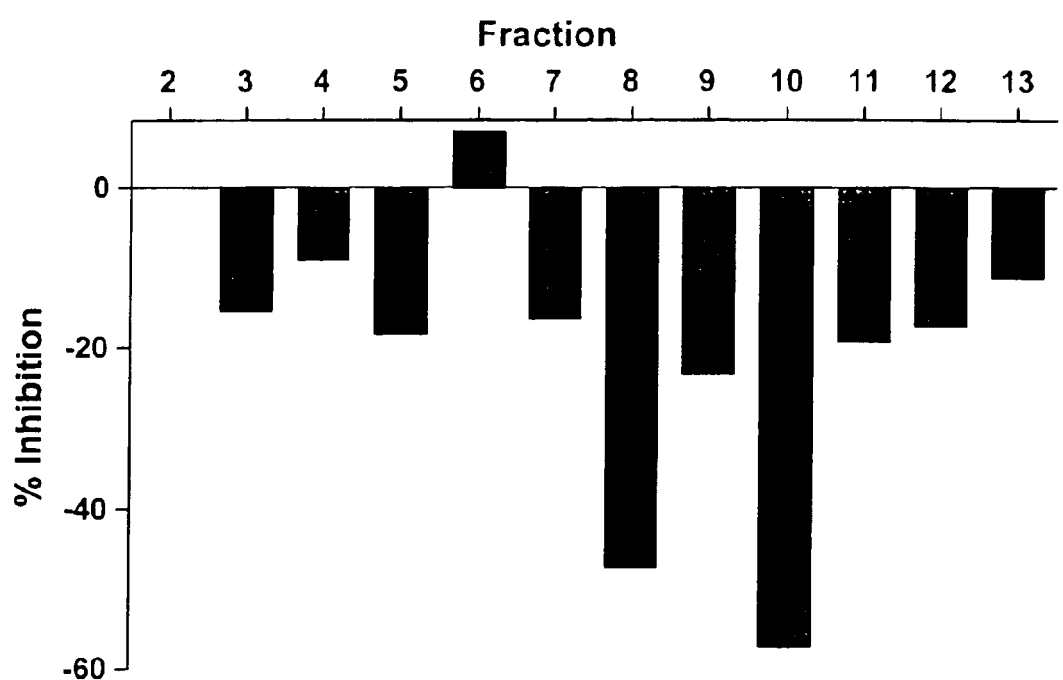
FIG. 5 shows GLP-1 binding activity of high performance liquid chromatography (HPLC) fractions of *Artemisia dracunculus* extract. Each fraction represented sequential 5 minute fractions tested at an equal concentration (10 $\mu$M with an assumed molecular weight of 300).
Figure 6:
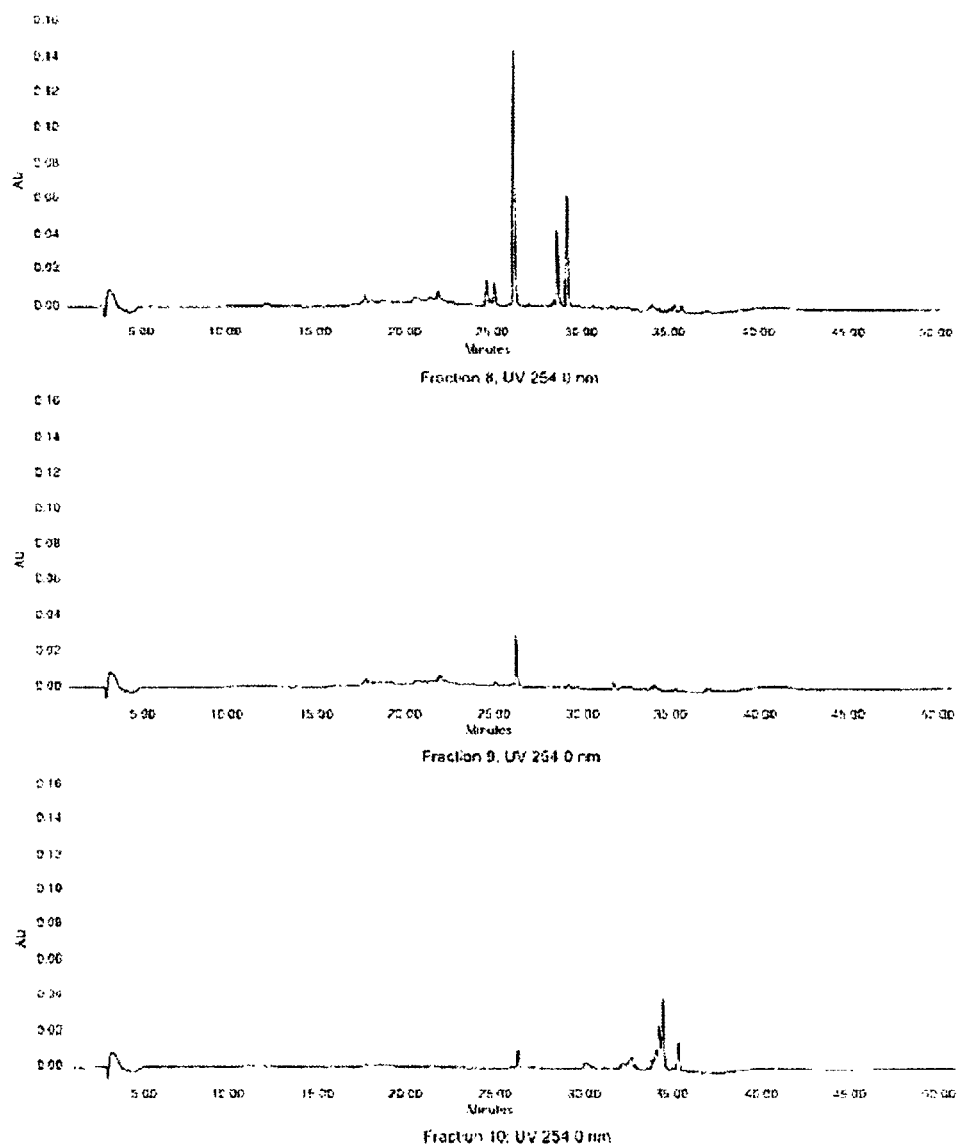
FIG. 6 shows liquid chromatography-mass spectometry (LC-MS) chromatograms revealing the biochemical profiles of *Artemisia dracunculus* extract corresponding to preparatory HPLC fractions 8–10 [8 (upper panel), 9 (middle panel), and 10 (lower panel)] from FIG. 5.

A GLP-1 binding assay was used for activity-guided fractionation of *Artemisia dracunculus* extract (see FIG. 5). The extract was dissolved in 60% ethanol and separated into 10 fractions of five minutes each using preparatory high performance liquid chromatography (HPLC). Each of the fractions was then reduced to dryness and tested at a concentration of 10 $\mu$g/ml. GLP-1 binding activity was increased by HPLC fractions 8 and 10 as demonstrated by an increase in negative percent inhibition (see FIG. 5).

Preparatory HPLC fractions 8–10 corresponded to the retention time window of 20–40 minutes in the LC-MS chromatograms presented in FIGS. 6–13. Therefore, this study suggested that peaks on the LC-MS chromatograms from 20–40 minutes may be of particular importance in extract activity. Changing peaks identify candidate active components of *Artemisia dracunculus*, but a useful characteristic of the extract is also its overall profile. Note that during this time period (20–40 minutes), some prominent peaks were found (see FIG. 6). However, all peaks in the *Artemisia dracunculus* extract profile contribute to the LC-MS profile, or fingerprint, of an extract in the biological function of the extract.

The activity of each HPLC fraction is also evaluated in vivo for its effect on GLP-1 binding activity and its ability to lower blood glucose in mammals. Fractions having activity are then further separated into individual components for the identification of active compounds in the extract having activity. Provided with this information, one of skill in the art can readily acquire corresponding profiles of inactive extracts for comparative studies to further characterize features of the profiles.

Figure 7A:
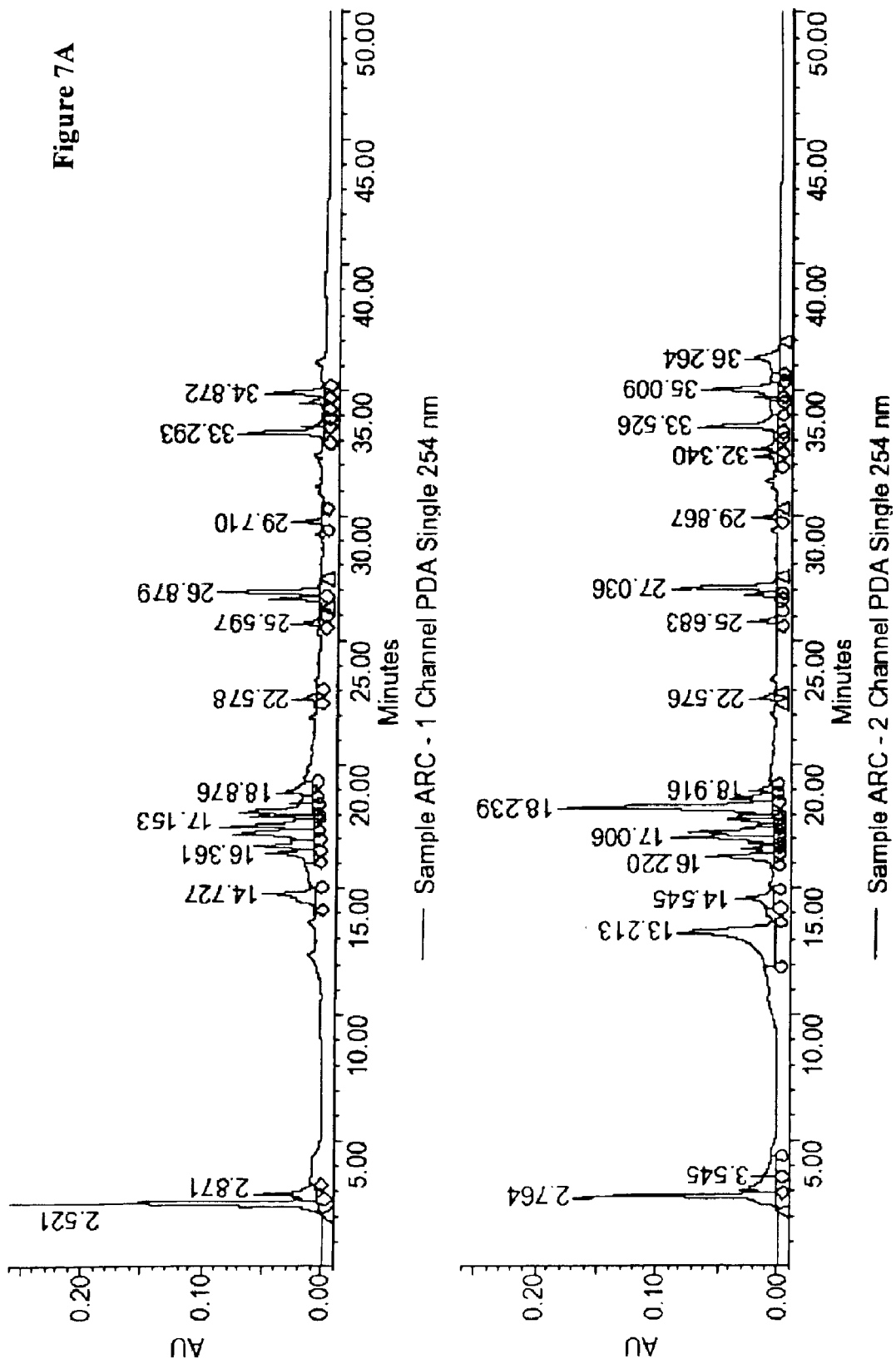
FIG. 7 shows a series of LC-MS chromatograms revealing the biochemical profiles of *Artemisia dracunculus* at various ages [7-day intervals after the seedling (about 14-days old) was transferred to large scale hydroponics (day 0)]. From top to bottom the six panels correspond to days 7, 14, 21, 28, 35, and 42, respectively, after the designated day 0.
Figure 7B:
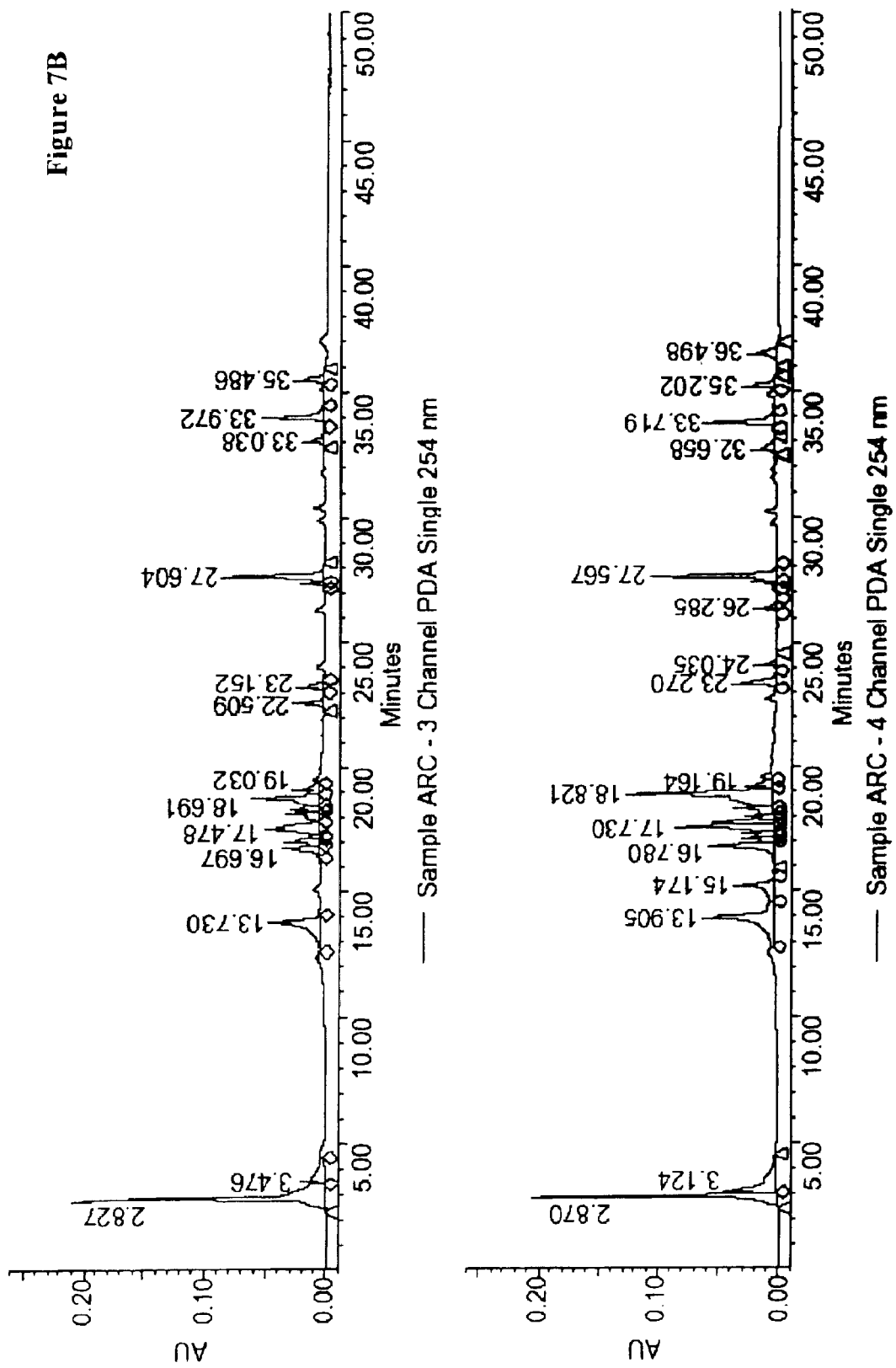
Figure 8:
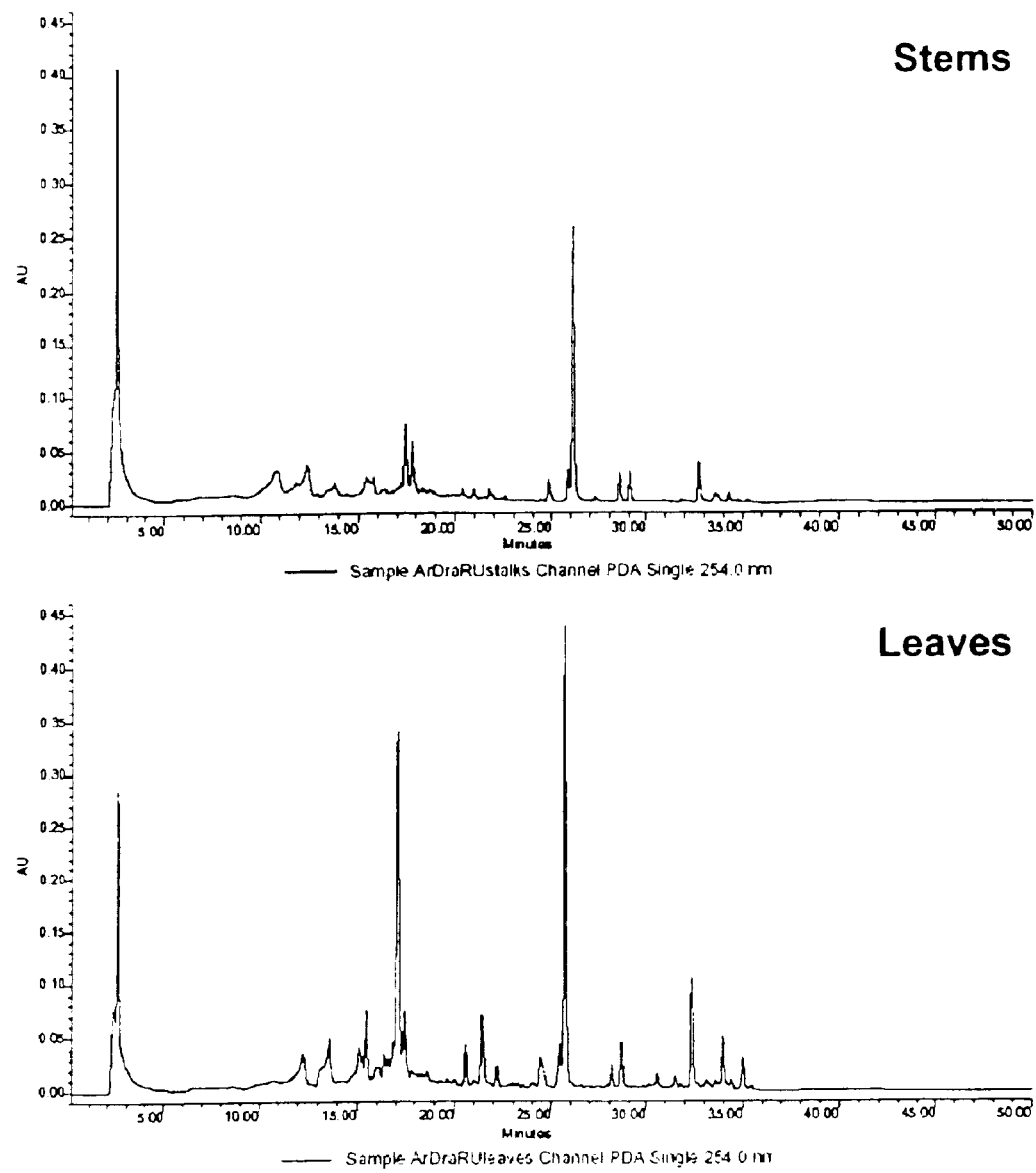
FIG. 8 shows LC-MS chromatograms revealing the biochemical profiles of *Artemisia dracunculus* stems (upper panel) and leaves (lower panel).
Figure 9:
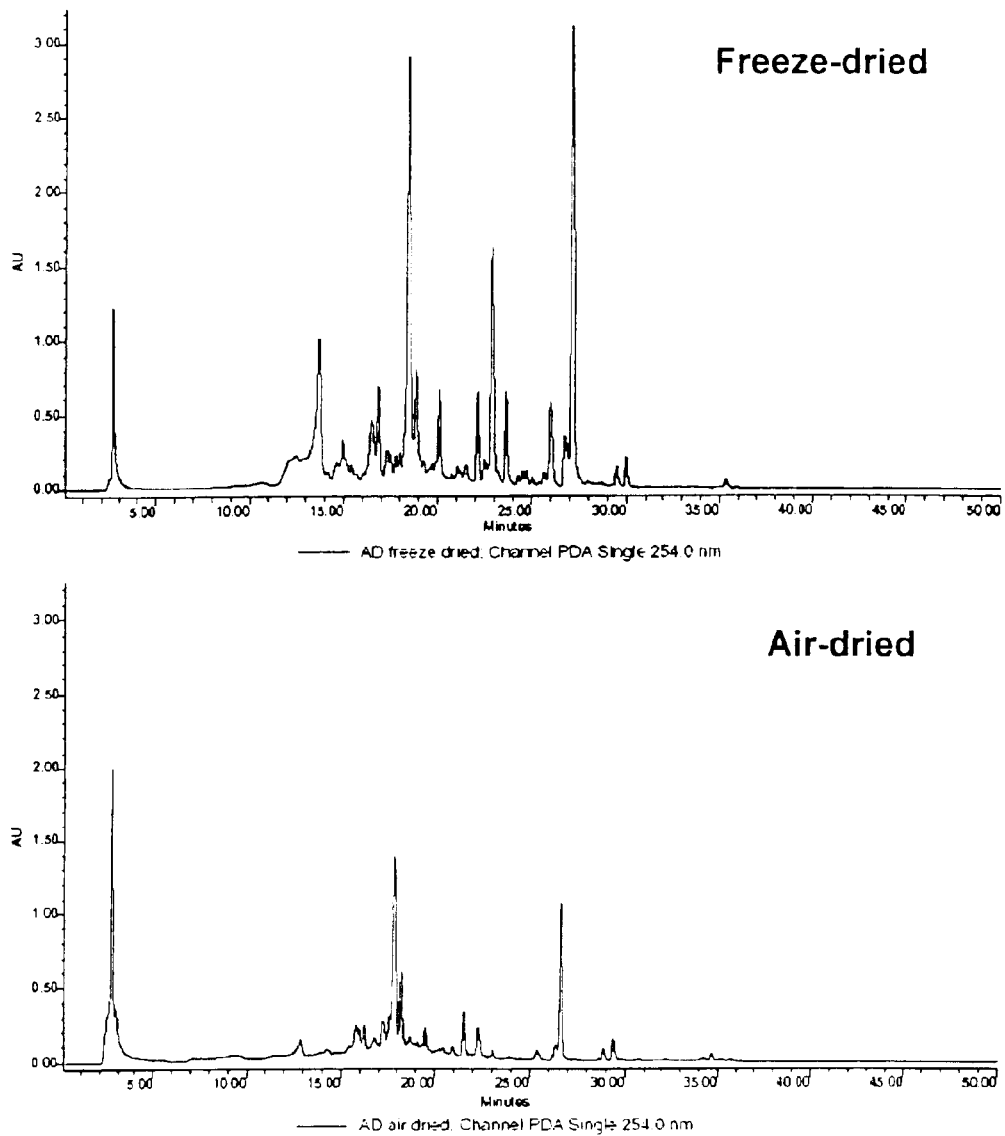
FIG. 9 shows LC-MS chromatograms revealing the biochemical profiles of *Artemisia dracunculus* extracts that were either freeze-dried (upper panel) or air-dried (lower panel).
Figure 10A:
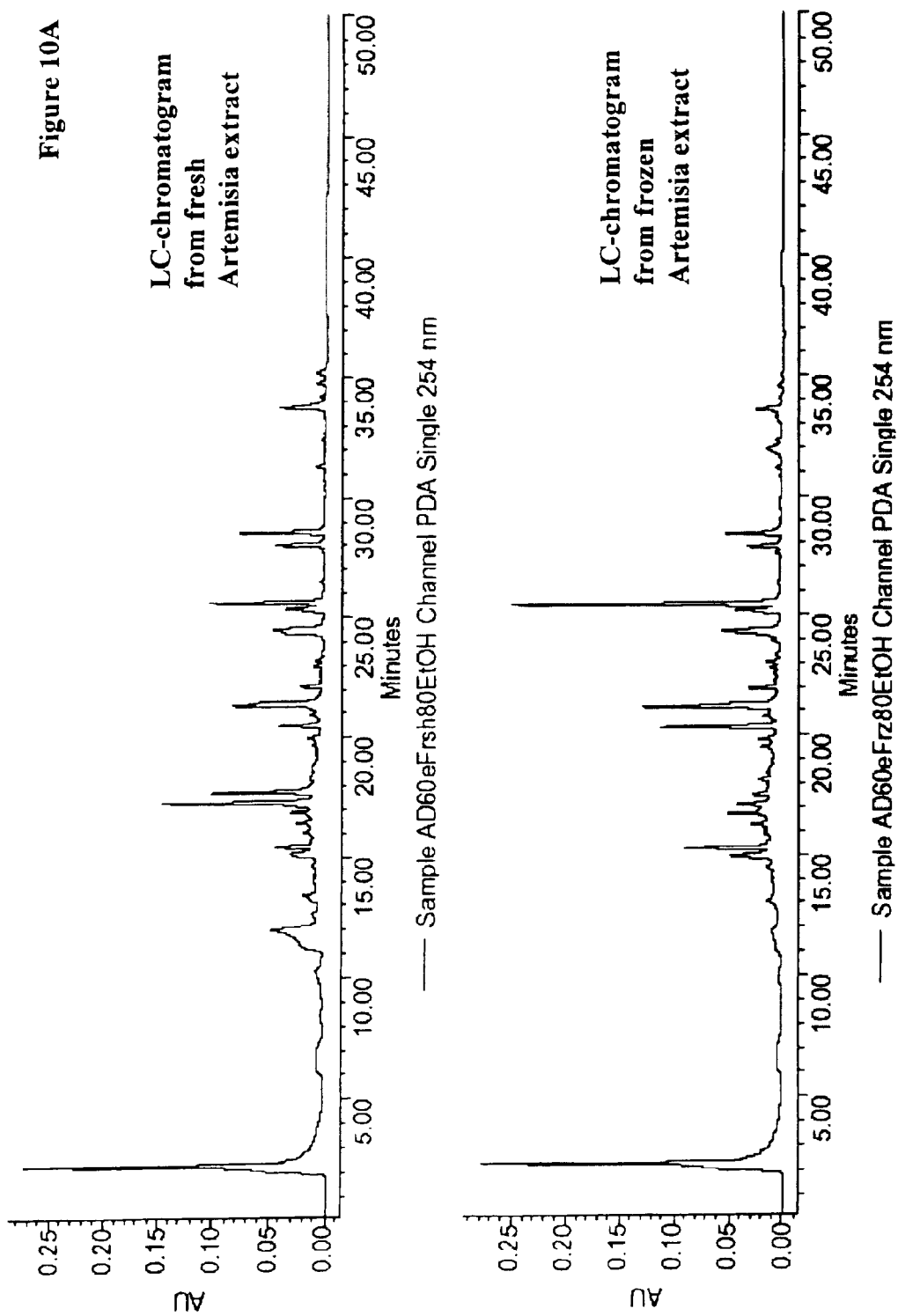
FIG. 10 shows LC-MS chromatograms revealing the biochemical profiles of non-macerated *Artemisia dracunculus* extracts from frozen material (left) or fresh material (right).
Figure 10B:
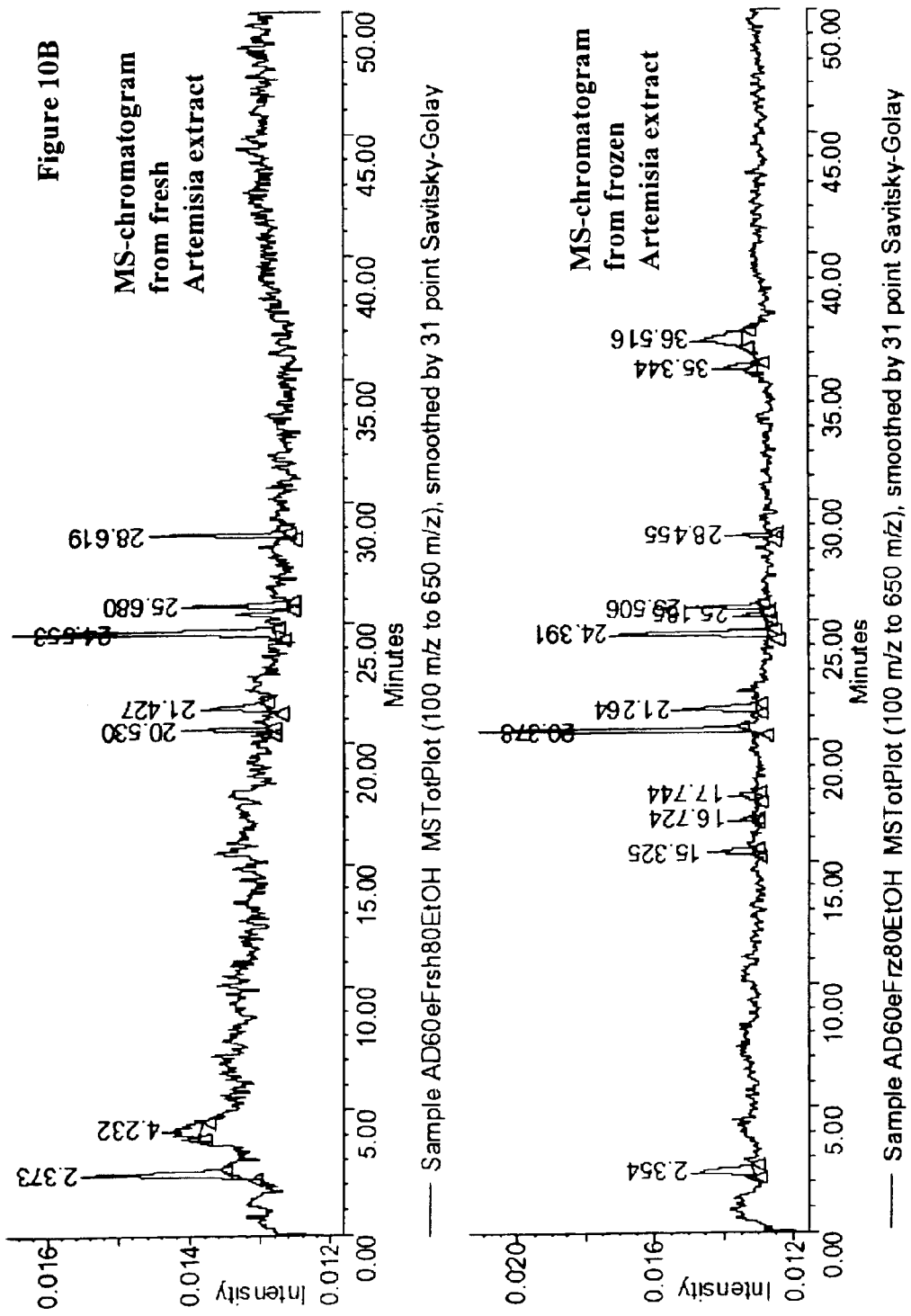

To examine extract profiles during growth and maturation of the *Artemisia dracunculus* plant, samples were taken at 7-day intervals for analysis by LC-MS (FIG. 7). The series of chromatograms shown in FIG. 7 were prepared from extracts of plants of days 7, 14, 21, 28, 35, and 42, respectively, after the seedling (about 14-days old) was transferred to large scale hydroponics (day 0). One of skill in the art will recognize that the peaks which appear before 5 minutes are generally regarded as sugars and/or breakdown products in the extracts coming through in the void volume of the column. As plants matured to a certain age (i.e. approximately 30–60 days old), extract quality increased. Mature plants (i.e. approximately 30–60 days old) provide increased mass as well as increased activity in the extract obtained relative to immature plants.

Moreover, as plants mature, they exhibit a generalized shift from a leaf-dominated biomass to a stem-dominated biomass. Extracts were prepared from separately processed stems and leaves in order to develop plant part-specific biochemical profiles. The preferred extract profile appears to be obtained from leaves of *Artemisia*, rather than stems (see FIG. 8).

In summary, the data have indicated that it may be more advantageous to process plants at a mature, but younger, age even if the older plants have greater overall mass, because the mass of younger plants is predominantly composed of leaves. Plants exhibited a preferred biochemical profile after the seedling stage when a certain degree of maturity had been reached (approximately 28 days). Young mature plants or new growth on older plants is preferred for extract preparation. This does not mean, however, that *Artemisia dracunculus* extracts cannot be processed from plants at any age. Also, other-plants, e.g., other species of *Artemisia* are also contemplated for use in the extracts of the present invention.

EXAMPLE 11

Extraction of *Artemisia dracunculus*

One procedure for preparing *Artemisia dracunculus* extracts was designed to provide a consistent method for comparing a variety of plants or plant treatments. In summary form, that procedure comprises of the following steps: (1) the plant material is freeze-dried and milled into a fine powder; (2) the powder is extracted in 60% ethanol; (3) the solids are removed by centrifugation; (4) ethanol is removed from the extract by rotary evaporation; and (5) water is removed from the extract by freeze-drying.

One of ordinary skill in the art would realize that the method may be modified appropriately, e.g., for the transition from a small-, or laboratory-, scale to a commercial-scale method. The drying process is unnecessary for extraction purposes. Fresh plant material provided the same biochemical profile as freeze-dried material, without the added cost of freeze-drying. Dried plant material did offer an advantage, however, in terms of transport and storage of the crop. Because the cost of freeze-drying is high and herbs are often air-dried in warm ovens, the extract profiles from both freeze-dried and air-dried plants were determined (see FIG. 9). The profiles obtained suggest that the activity of the extract from air-dried plants may be lower than the activity of freeze-dried extracts, as seen by the increase in breakdown products in the air-dried profile (see peak before 5 min.) as well as the overall decrease in the number as well as height (AU) of peaks in the air-dried profile as compared to that of the freeze-dried profile.

One approach to achieving a high efficiency of extraction is to mill dried plant material into a powder. Milling is not an expensive processing step, but does add to the overall cost of processing. The water content of fresh material makes milling relatively difficult and ineffective, but fresh material can be macerated directly in the fluid or solvent with which it will be extracted. Alternatively, an extended extraction time, especially at elevated temperatures, may provide comparable yields from macerated and non-macerated plant materials, such as *Artemisia* materials. Most commercial processors also have the capacity to percolate the menstruum during the extraction process, which tends to result in higher yields of plant materials (e.g., *Artemisia dracunculus*) in extracts. Therefore, milling is not a required processing step.

In using fresh plant material for the preparation (i.e., processing) of plant extracts (e.g., *Artemisia dracunculus* extracts), one must consider transport and storage. There is an advantage to having growers and processors within close proximity. It is possible to coordinate the harvest of crops, such as *Artemisia dracunculus*, from hydroponic greenhouses with the batch processing of the plant material at a commercial facility. An alternative is to freeze the crops for transport and storage. Freezing does offer another advantage in that the extraction of frozen plant material is more efficient than fresh plant material. *Artemisia dracunculus* extract activity may be greater from frozen plant material than from fresh material, as indicated by the LC-chromatogram and MS-chromatogram profiles obtained (see FIG. 10). The LC chromatographic profiles in the left panel of FIG. 10 were detected by photodiode array and the chromatographic profiles in the right panel of FIG. 10 were detected by mass spectometry (MS; total ion chromatography).

Figure 11B:
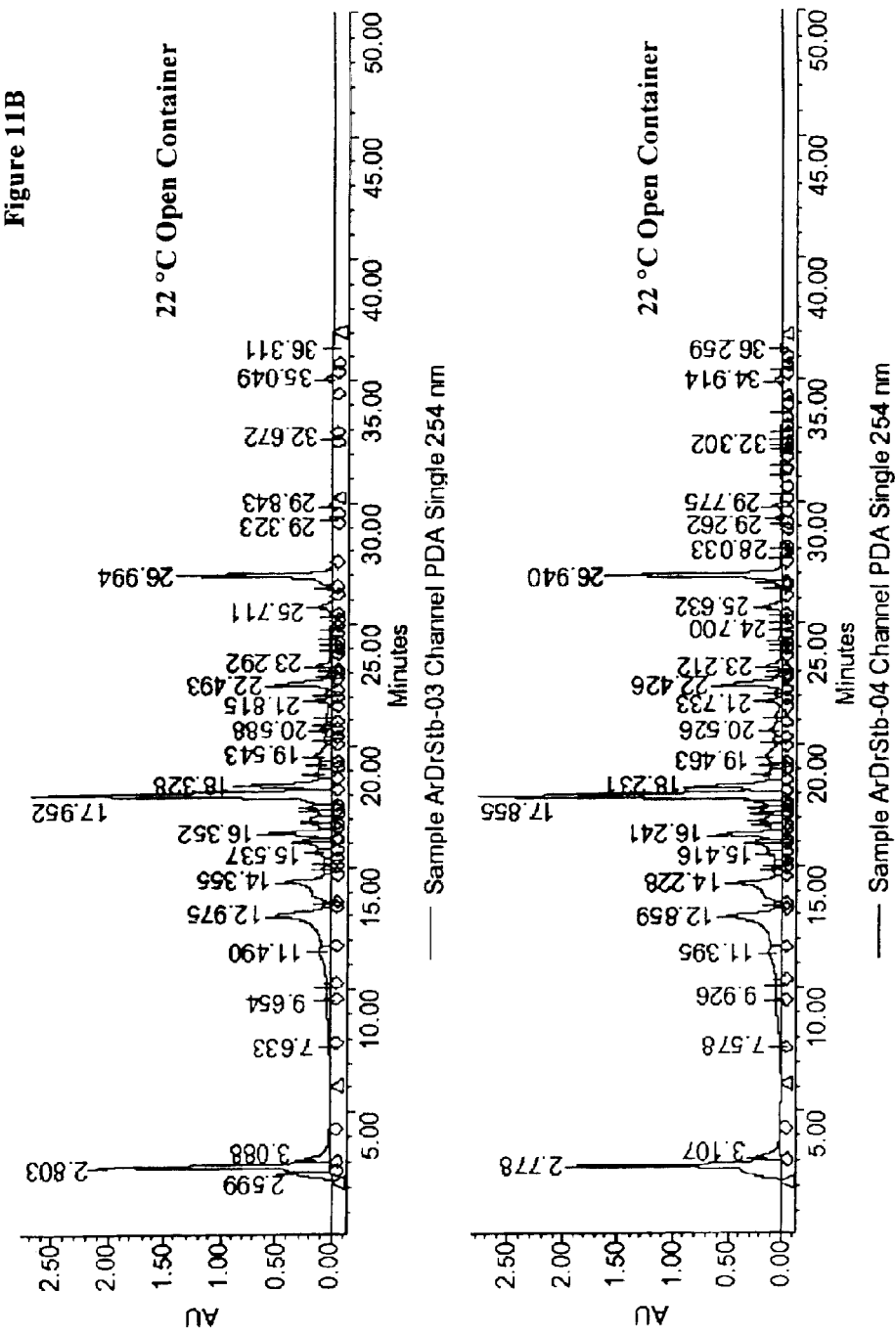
FIG. 11 shows LC-MS chromatograms revealing the biochemical profiles of *Artemisia dracunculus* extracts maintained under a variety of conditions. From top to bottom the conditions were: −20° C. freezer, 22° C. open container, 22° C. desiccators, and 37° C. open oven.
Figure 12:
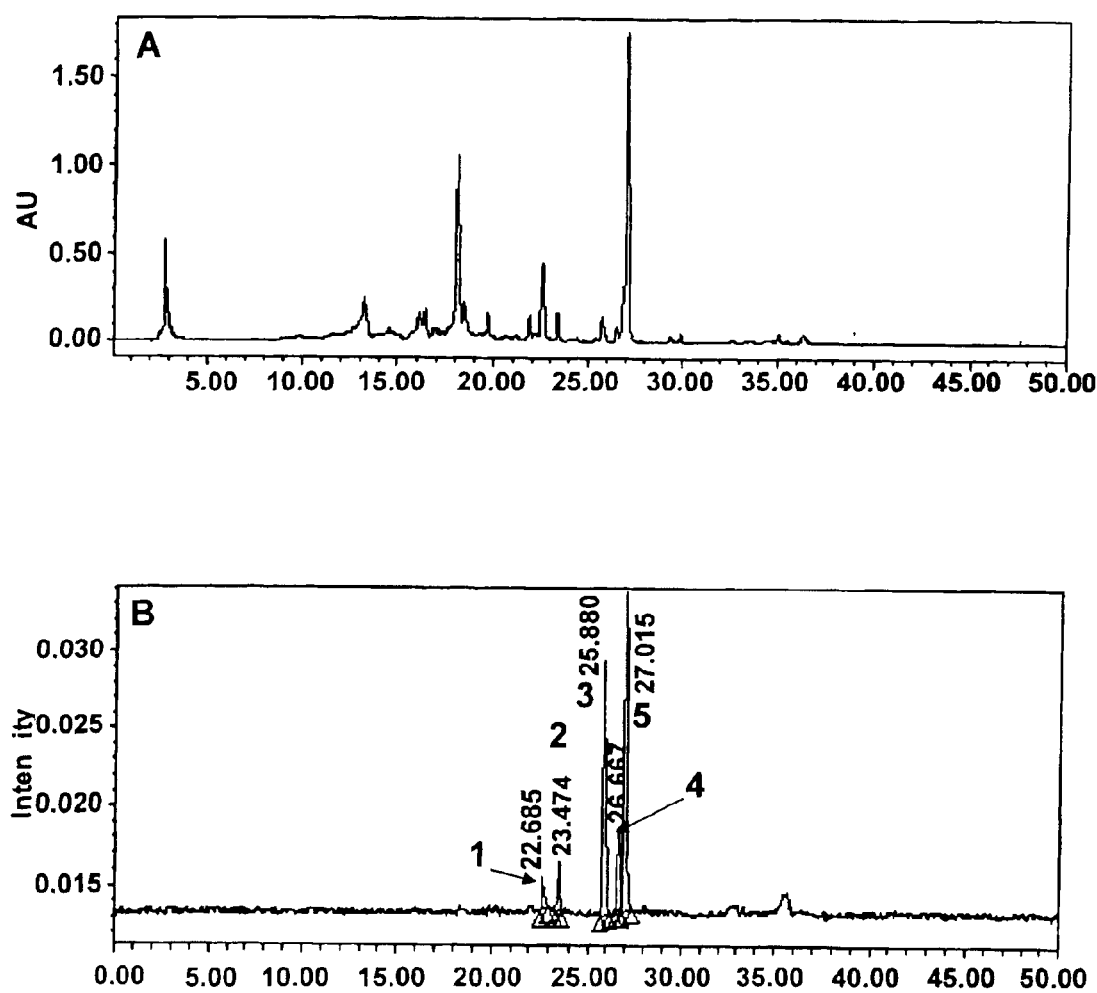
FIG. 12 presents the results of analyzing an *Artemisia dracunculus* extract by UV chromatogram (254 nm) (panel A) and mass spectral total ion chromatogram (panel B). The putative identities of the primary constituents of the peaks in panel B correspond to the numbers shown. Peak identification of profile B: 1) mixture of either capillarisin or tetrahydroxymethoxy flavanone with an umbelliferone derivative, 2) diterpene, 3) sakuranin derivative or trihydroxymethoxy flavanone, 4) diterpene, and 5) primarily trihydroxy flavanone in a composite peak having at least three components.
Figure 13:
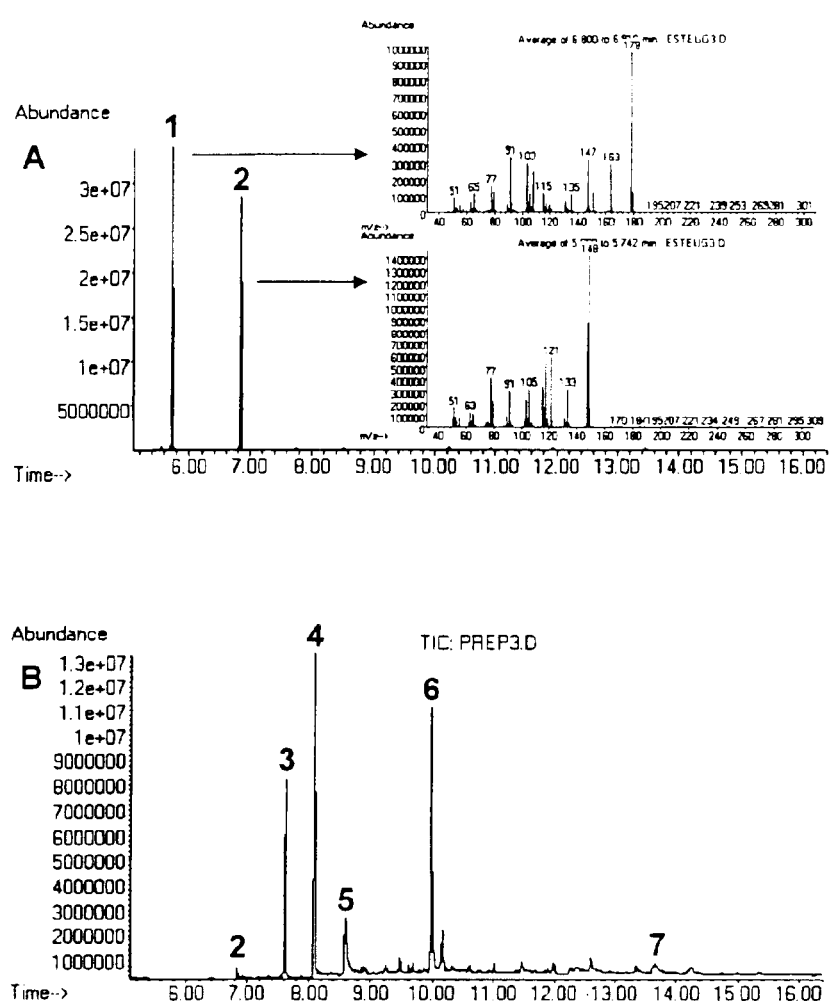
FIG. 13 presents the results of analyzing an *Artemisia dracunculus* extract for estragole and methyl eugenol. Panel A is the total ion chromatogram of standards of estragole (1) and methyl eugenol (2) with the mass spectral fragmentations for each compound. Panel B is the total ion chromatogram of a batch of *Artemisia dracunculus* extract with putative identifications of the constituents of the primary peaks. Peak identification of panel B: (1) estragole undetectable and not shown), 2) methyl eugenol, 3) 1,2,3-trimethoxy-5-(2-prophenyl) benzene, 4) trans isoelemicin, 5) methyl umbelliferone, 6) phytol, and 7) 4,5-dihydroxy-7-methoxyflavanone.

The stability of *Artemisia dracunculus* extract was examined under a variety of different storage conditions (see FIG. 11). The chromatograms shown in FIG. 11 represent a sample of *Artemisia dracunculus* extract divided into four parts, with each part receiving one of the following subsequent treatments: stored at −20° C. (in a freezer), stored at 22° C. (room temperature) in an open container, stored at 22° C. (room temperature) in a desiccator, or stored at 37° C. (an elevated temperature) in an open container. All conditions were closely controlled for the evaluation of stability by carrying out the studies in closed containers that exposed the test substance to lower amounts of oxygen and humidity. These chromatograms were obtained after 7 months of storage and all appear to be identical to the chromatograms obtained from the sample at the beginning of the study. These experiments demonstrated that the *Artemisia dracunculus* extract is very stable under a variety of experimental storage conditions over a long period of time.

EXAMPLE 12

LC-MS and GC-MS Analyses of *Artemisia dracunculus* Extract

The *Artemisia dracunculus* extract was prepared and tested for quality, consistency, and safety by both LC-MS and GC-MS. Typical LC-MS chromatograms were prepared and analyzed, and the putative identities of the primary peaks listed with corresponding numbers were determined (see FIG. 12). Primary peak identities were determined by spectral matching with the Wiley library of mass spectra and cannot be considered as absolute identities. Putative compounds identified in *Artemisia dracunculus* extract were identified as follows: 1) a mixture of either capillarisin, or tetrahydroxy-methoxy flavanone with an umbelliferone derivative; 2) diterpene; 3) sakuranin derivative, or trihydroxy-methoxy flavanone; 4) diterpene; and 5) mainly trihydroxy flavanone. The peaks identified as diterpenes match with several diterpene-like compounds.

GC-MS analysis of *Artemisia dracunculus* extract was performed primarily for reasons of safety in ensuring the absence of toxic principals. The method by which *Artemisia dracunculus* extract was prepared was not designed to retain the volatile principals of the plant and most of the compounds present in the GC-MS analyses, therefore, were present in low abundance (see GC-MS chromatograms in FIG. 13). The total ion chromatogram (see FIG. 13, panel A) consisted of a mixed standard of estragole (1) and methyl eugenol (2) with the mass spectral fragmentations for each compound also provided in the figure. The total ion chromatogram of *Artemisia dracunculus* extract (see FIG. 13, panel B) identified the following putative compounds in the primary peaks: (1) estragole standard was undetectable and not shown); 2) methyl eugenol; 3)1,2,3-trimethoxy-5-(2-prophenyl)benzene; 4) trans isoelemicin; 5) methyl umbelliferone; 6) phytol; and 7) 4,5-dihydroxy-7-methoxyflavanone. Estragole was absent in this chromatogram while methyl eugenol was present, but at only a trace amount (25-fold reduction relative to raw extract).

It is evident from the analyses of both the LC-MS and GC-MS chromatograms that *Artemisia dracunculus* extract consists of several different compounds, some of which have been identified as described above.

EXAMPLE 13

Extract Pharmaceutical Compositions and Administration

Therapeutic pharmaceutical compositions are within the scope of the present invention. Such pharmaceutical compositions may comprise an effective dose of a plant extract such as a mildly polar extract of *Artemisia dracunculus*, in admixture with a pharmaceutically or physiologically acceptable formulation agent selected for suitability with the mode of administration. Exemplary pharmaceutical compositions may comprise an effective dose of one or more plant extracts such as one or more mildly polar extracts of *Artemisia dracunculus*, in admixture with a pharmaceutically or physiologically acceptable formulation agent selected for suitability with the mode of administration. Acceptable formulation materials preferably are nontoxic to recipients at the dosages and concentrations employed.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen sulfite); buffers (such as borate, bicarbonate, Tris-HCl, citrates, phosphates, other organic acids and salts thereof); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides and other carbohydrates (such as glucose, mannose, or dextrins); proteins (such as serum albumin, gelatin or immunoglobulins); coloring; flavoring and/or diluting agents; emulsifying agents; hydrophilic polymers (such as, polyvinylpyrrolidone); low molecular weight polypeptides; salt-forming counterions [such as alkali metal ions, alkaline earth metal ions, halogen ions, organic cations, organic ions, complex ions and any other counterion known in the art (preferably sodium)]; preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, or polysorbates such as polysorbate 20, polysorbate 80, triton, tromethamine, lecithin, cholesterol, tyloxapal); stability enhancing agents (sucrose or sorbitol); tonicity enhancing agents [such as alkali metal halides (preferably sodium or potassium chloride), mannitol, or sorbitol]; delivery vehicles; diluents; excipients and/or pharmaceutical adjuvants. (*Remington's Pharmaceutical Sciences*, 18th Edition, A. R. Gennaro, ed., Mack Publishing Company, 1990).

The optimal pharmaceutical composition is determined by one skilled in the art depending upon, for example, the intended route of administration, delivery format, and desired dosage. See for example, *Remington's Pharmaceutical Sciences*. Such compositions may influence the physical state, stability, rate of in vivo release, and rate of in vivo clearance of the plant extracts, such as the mildly polar extracts of plants such as *Artemisia dracunculus*.

The primary vehicle or carrier in a pharmaceutical composition is either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0–8.5, or acetate buffer of about pH 4.0–5.5, which may further include sorbitol or a suitable substitute therefor. In some embodiments of the present invention, mildly polar plant extract compositions may be prepared for storage by mixing the selected composition having the desired degree of purity with optional formulation agents (*Remington's Pharmaceutical Sciences*) in the form of a lyophilized cake or an aqueous solution. Further, the extract product may be formulated as a lyophilizate using appropriate excipients such as sucrose.

The pharmaceutical compositions of the mildly polar extracts may be selected for parenteral delivery. Alternatively, the compositions may be selected for delivery through the respiratory tract or digestive tract, such as orally or through a nasogastric tube. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of about 5 to about 8.

When parenteral administration is contemplated, the therapeutic compositions for use in this invention may be in the form of a pyrogen-free, parenterally acceptable aqueous solution comprising the desired plant extract in a pharmaceutically acceptable vehicle. A particularly suitable vehicle for parenteral injection is sterile distilled water in which the extract is formulated as a sterile, isotonic solution, properly preserved. Yet another preparation may involve the formulation of the desired molecule with an agent, such as injectable microspheres, bio-erodable particles, polymeric compounds (polylactic acid, polyglycolic acid), beads, or liposomes, which provides for the controlled and/or sustained release of the product which may then be delivered via a depot injection. Hyaluronic acid may also be used, and this may have the effect of promoting sustained duration in the circulation. Other suitable means for the introduction of the desired molecule include implantable drug delivery devices.

As noted above, it is contemplated that certain formulations may be administered orally. In some embodiments of the present invention, mildly polar extracts of a plant such as *Artemisia dracunculus* may be formulated for oral delivery with or without those carriers customarily used in the compounding of solid dosage forms such as tablets and capsules. For example, a capsule may be designed to release the active portion of the formulation at the point in the gastrointestinal tract where bioavailability is maximized and pre-systemic degradation is minimized. Additional agents may be included to facilitate absorption of the mildly polar plant extracts. Diluents, flavorings, low melting point waxes, vegetable oils, lubricants, suspending agents, tablet disintegrating agents, and binders may also be employed.

Another pharmaceutical composition may involve an effective quantity of an extract of a plant such as *Artemisia dracunculus* in a mixture with a non-toxic excipient which is suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving extracts of plants such as *Artemisia dracunculus* in sustained- or controlled-delivery formulations. Products for formulating a variety of other sustained- or controlled-delivery compositions include liposome carriers, bio-erodable microparticles or porous beads and depot injections, and others, all of which are known to those skilled in the art. See for example, PCT/US93/00829, which describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al, Biopolymers, 22:547–556, 1983), poly (2-hydroxyethyl-methacrylate) (Langer et al., *J. Biomed. Mater. Res.*, 15:167–277, 1981) and Langer et al., *Chem. Tech.*, 12:98–105, 1982), ethylene vinyl acetate (Langer et al., supra) or poly-D(-)-3-hydroxybutyric acid (EP 133,988). Liposomes may be prepared by any of several methods known in the art. See, e.g., Eppstein et al., *Proc. Natl. Acad. Sci. USA*, 82:3688–3692,1985; EP 36,676; EP 88,046; EP 143,949.

The pharmaceutical-composition of an extract of a plant such as *Artemisia dracunculus* to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

Numerous modifications and variations of the present invention are possible in view of the above teachings and are within the scope of the invention. The entire disclosure of all publications cited herein are hereby incorporated by reference.

What is claimed:

1. A method of treating Type 2 diabetes in a mammal comprising administering an effective dose of a mildly polar extract of *Artemisia dracunculus* to a mammal in need thereof.

2. The method of claim 1, wherein administering said *Artemisia dracunculus* extract decreases blood glucose level in said mammal.

3. The method of claim 1, wherein administering said *Artemisia dracunculus* extract increases glucagon-like peptide-1 (GLP-1) activity in said mammal.

4. The method of claim 1, wherein administering said *Artemisia dracunculus* extract increases the binding between GLP-1 and GLP-1 receptor in said mammal.

5. The method of claim 1, wherein administering said *Artemisia dracunculus* extract decreases insulin resistance in said mammal.

6. The method of claim 1, wherein administering said *Artemisia dracunculus* extract increases the in vivo conversion of glucose to glycogen in said mammal.

7. The method of claim 1, wherein administering said *Artemisia drecunculus* increases expression of insulin receptor substrate-2 (IRS-2) polypeptide in said mammal.

8. The method of claim 1, wherein administering said *Artemisia dracunculus* extract increases insulin-stimulated glucose uptake in said mammal.

9. The method of claim 1, wherein administering said *Artemisia dracunculus* extract decreases hepatic glucose output in said mammal.

* * * * *

UNITED STATES PATENT AND TRADEMARK OFFICE
CERTIFICATE OF CORRECTION

PATENT NO. : 6,893,627 B2
DATED : May 17, 2005
INVENTOR(S) : Ribnicky et al.

It is certified that error appears in the above-identified patent and that said Letters Patent is hereby corrected as shown below:

Title page,
Item [75], Inventors, "Plainsboro" should be -- North Branch --.

Column 27,
Line 15, "glucagons-like" should be -- glucagon-like --.

Column 28,
Line 8, "drecunculus" should be -- dracunculus --.

Signed and Sealed this

Thirtieth Day of August, 2005

JON W. DUDAS
*Director of the United States Patent and Trademark Office*